(12) United States Patent
Alexander

(10) Patent No.: US 12,295,584 B2
(45) Date of Patent: *May 13, 2025

(54) SYSTEMS AND METHODS FOR DELIVERING AN IMPLANTABLE DEVICE

(71) Applicant: EDWARDS LIFESCIENCES CORPORATION, Irvine, CA (US)

(72) Inventor: Miles D. Alexander, Menlo Park, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/530,731

(22) Filed: Dec. 6, 2023

(65) Prior Publication Data
US 2024/0099722 A1 Mar. 28, 2024

Related U.S. Application Data

(60) Continuation of application No. 16/997,793, filed on Aug. 19, 2020, now Pat. No. 11,864,771, which is a
(Continued)

(51) Int. Cl.
*A61B 17/12* (2006.01)
*A61B 17/00* (2006.01)

(52) U.S. Cl.
CPC .. *A61B 17/12122* (2013.01); *A61B 17/12172* (2013.01); *A61B 17/12177* (2013.01);
(Continued)

(58) Field of Classification Search
CPC ........ A61B 17/12122; A61B 17/12172; A61B 17/12177; A61B 2017/0053; A61B 2017/12054; A61B 2217/007
See application file for complete search history.

(56) References Cited

U.S. PATENT DOCUMENTS

| 3,409,013 A | 11/1968 | Berry |
| 3,472,230 A | 10/1969 | Fogarty |

(Continued)

FOREIGN PATENT DOCUMENTS

| CA | 2304325 C | 5/2008 |
| DE | 2246526 A1 | 3/1973 |

(Continued)

OTHER PUBLICATIONS

Andersen, et al., "Transluminal implantation of artificial heart valves. Description of a new expandable aortic valve and initial results with implantation by catheter technique in closed chest pigs." European Heart Journal (1992), 13, 704-708.
(Continued)

*Primary Examiner* — Kelly J Bekker
*Assistant Examiner* — Andrew P. Restaino
(74) *Attorney, Agent, or Firm* — Thomas C. Richardson

(57) ABSTRACT

A method of preparing a ventricular partitioning device for implantation using a delivery system can include coupling the ventricular partitioning device to a delivery catheter, loading the ventricular partitioning device and a portion of the delivery catheter into a sleeve and creating a liquid-tight seal between a portion of the sleeve and the delivery catheter, coupling a distal end of the sleeve to a guide catheter, and delivering fluid through at least one of the first fluid delivery port or the second fluid delivery port. The method can be performed with the delivery catheter or the sleeve having a first fluid delivery port positioned thereon. The method can be with the guide catheter having a second fluid delivery port positioned thereon.

20 Claims, 18 Drawing Sheets

Related U.S. Application Data division of application No. 15/559,680, filed as application No. PCT/US2016/022863 on Mar. 17, 2016, now Pat. No. 10,751,064.

(60) Provisional application No. 62/136,248, filed on Mar. 20, 2015.

(52) U.S. Cl.
CPC ........... *A61B 2017/0053* (2013.01); *A61B 2017/12054* (2013.01); *A61B 2217/007* (2013.01)

(56) References Cited

U.S. PATENT DOCUMENTS

| | | |
|---|---|---|
| 3,548,417 A | 12/1970 | Kischer et al. |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,739,402 A | 6/1973 | Cooley et al. |
| 3,755,823 A | 9/1973 | Hancock |
| 4,011,947 A | 3/1977 | Sawyer |
| 4,035,849 A | 7/1977 | Angell et al. |
| 4,056,854 A | 11/1977 | Boretos et al. |
| 4,079,468 A | 3/1978 | Liotta et al. |
| 4,106,129 A | 8/1978 | Carpentier et al. |
| 4,204,283 A | 5/1980 | Bellhouse et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,340,977 A | 7/1982 | Brownlee et al. |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,477,930 A | 10/1984 | Totten et al. |
| 4,490,859 A | 1/1985 | Black et al. |
| 4,535,483 A | 8/1985 | Klawitter et al. |
| 4,553,545 A | 11/1985 | Maass et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,865,600 A | 9/1989 | Carpentier et al. |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,232,446 A | 8/1993 | Arney |
| 5,266,073 A | 11/1993 | Wall |
| 5,282,847 A | 2/1994 | Trescony et al. |
| 5,295,958 A | 3/1994 | Shturman |
| 5,326,371 A | 7/1994 | Love et al. |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,522 A | 5/1995 | Trott |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,185 A | 1/1997 | Kilmer et al. |
| 5,599,305 A | 2/1997 | Hermann et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,697,382 A | 12/1997 | Love et al. |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,906,619 A | 5/1999 | Olson et al. |
| 5,925,063 A | 7/1999 | Khosravi |
| 5,957,949 A | 9/1999 | Leonhardt et al. |
| 5,968,068 A | 10/1999 | Dehdashtian et al. |
| 6,027,525 A | 2/2000 | Suh et al. |
| 6,042,607 A | 3/2000 | Williamson et al. |
| 6,086,612 A | 7/2000 | Jansen |
| 6,113,631 A | 9/2000 | Jansen |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,040 B1 | 6/2001 | Inderbitzen et al. |
| 6,245,102 B1 | 6/2001 | Jayaraman |
| 6,251,093 B1 | 6/2001 | Valley et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,306,141 B1 | 10/2001 | Jervis |
| 6,312,465 B1 | 11/2001 | Griffin et al. |
| 6,350,277 B1 | 2/2002 | Kocur |
| 6,358,277 B1 | 3/2002 | Duran |
| 6,379,372 B1 | 4/2002 | Dehdashtian et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |

(56) References Cited

U.S. PATENT DOCUMENTS

| | | |
|---|---|---|
| 6,482,228 B1 | 11/2002 | Norred |
| 6,488,704 B1 | 12/2002 | Connelly et al. |
| 6,527,800 B1 | 3/2003 | McGuckin et al. |
| 6,527,979 B2 | 3/2003 | Constantz et al. |
| 6,540,782 B1 | 4/2003 | Snyders |
| 6,569,196 B1 | 5/2003 | Vesely |
| 6,575,959 B1 | 6/2003 | Sarge et al. |
| 6,582,462 B1 | 6/2003 | Andersen et al. |
| 6,605,112 B1 | 8/2003 | Moll et al. |
| 6,610,088 B1 | 8/2003 | Gabbay |
| 6,629,534 B1 | 10/2003 | St. Goar et al. |
| 6,676,698 B2 | 1/2004 | McGuckin et al. |
| 6,695,878 B2 | 2/2004 | McGuckin et al. |
| 6,712,836 B1 | 3/2004 | Berg et al. |
| 6,716,207 B2 | 4/2004 | Farnholtz |
| 6,729,356 B1 | 5/2004 | Baker et al. |
| 6,730,118 B2 | 5/2004 | Spenser et al. |
| 6,733,525 B2 | 5/2004 | Yang et al. |
| 6,746,422 B1 | 6/2004 | Noriega et al. |
| 6,749,560 B1 | 6/2004 | Konstorum et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,830,584 B1 | 12/2004 | Seguin |
| 6,875,231 B2 | 4/2005 | Anduiza et al. |
| 6,893,460 B2 | 5/2005 | Spenser et al. |
| 6,908,481 B2 | 6/2005 | Cribier |
| 6,974,476 B2 | 12/2005 | McGuckin et al. |
| 7,018,406 B2 | 3/2006 | Seguin et al. |
| 7,186,265 B2 | 3/2007 | Sharkawy et al. |
| 7,192,440 B2 | 3/2007 | Andreas et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,381,210 B2 | 6/2008 | Zarbatany et al. |
| 7,381,219 B2 | 6/2008 | Salahieh et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,530,253 B2 | 5/2009 | Spenser et al. |
| 7,553,324 B2 | 6/2009 | Andreas et al. |
| 7,579,381 B2 | 8/2009 | Dove |
| 7,585,321 B2 | 9/2009 | Cribier |
| 7,618,446 B2 | 11/2009 | Andersen et al. |
| 7,621,948 B2 | 11/2009 | Herrmann et al. |
| 7,704,222 B2 | 4/2010 | Wilk et al. |
| 7,736,327 B2 | 6/2010 | Wilk et al. |
| 7,748,389 B2 | 7/2010 | Salahieh et al. |
| 7,753,949 B2 | 7/2010 | Lamphere et al. |
| 7,806,919 B2 | 10/2010 | Bloom et al. |
| 7,824,443 B2 | 11/2010 | Salahieh et al. |
| 7,837,727 B2 | 11/2010 | Goetz et al. |
| 7,892,281 B2 | 2/2011 | Seguin et al. |
| 7,914,569 B2 | 3/2011 | Nguyen et al. |
| 7,914,575 B2 | 3/2011 | Guyenot et al. |
| 7,959,672 B2 | 6/2011 | Salahieh et al. |
| 7,972,378 B2 | 7/2011 | Tabor et al. |
| 7,981,151 B2 | 7/2011 | Rowe |
| 7,993,392 B2 | 8/2011 | Righini et al. |
| 7,993,394 B2 | 8/2011 | Hariton et al. |
| 8,007,992 B2 | 8/2011 | Tian et al. |
| 8,016,877 B2 | 9/2011 | Seguin et al. |
| 8,029,556 B2 | 10/2011 | Rowe |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,092,520 B2 | 1/2012 | Quadri |
| 8,092,521 B2 | 1/2012 | Figulla et al. |
| 8,109,996 B2 | 2/2012 | Stacchino et al. |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,932 B2 | 5/2012 | Bourang et al. |
| 8,167,934 B2 | 5/2012 | Styrc et al. |
| 8,182,530 B2 | 5/2012 | Huber |
| 8,206,437 B2 | 6/2012 | Bonhoeffer et al. |
| 8,216,174 B2 | 7/2012 | Wilk et al. |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,236,045 B2 | 8/2012 | Benichou et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,313,525 B2 | 11/2012 | Tuval et al. |
| 8,317,858 B2 | 11/2012 | Straubinger et al. |
| 8,323,335 B2 | 12/2012 | Rowe et al. |
| 8,337,541 B2 | 12/2012 | Quadri et al. |
| 8,353,953 B2 | 1/2013 | Giannetti et al. |
| 8,398,704 B2 | 3/2013 | Straubinger et al. |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,416,643 B2 | 4/2013 | Magee |
| 8,444,689 B2 | 5/2013 | Zhang |
| 8,449,599 B2 | 5/2013 | Chau et al. |
| 8,454,685 B2 | 6/2013 | Hariton et al. |
| 8,460,368 B2 | 6/2013 | Taylor et al. |
| 8,460,370 B2 | 6/2013 | Zakay et al. |
| 8,470,023 B2 | 6/2013 | Eidenschink et al. |
| 8,470,028 B2 | 6/2013 | Thornton et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,491,650 B2 | 7/2013 | Wiemeyer et al. |
| 8,500,733 B2 | 8/2013 | Watson |
| 8,500,798 B2 | 8/2013 | Rowe et al. |
| 8,511,244 B2 | 8/2013 | Holecek et al. |
| 8,512,401 B2 | 8/2013 | Murray et al. |
| 8,518,096 B2 | 8/2013 | Nelson |
| 8,518,106 B2 | 8/2013 | Duffy et al. |
| 8,562,663 B2 | 10/2013 | Mearns et al. |
| 8,579,963 B2 | 11/2013 | Tabor |
| 8,579,964 B2 | 11/2013 | Lane et al. |
| 8,591,570 B2 | 11/2013 | Revuelta et al. |
| 8,617,236 B2 | 12/2013 | Paul et al. |
| 8,640,521 B2 | 2/2014 | Righini et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,202 B2 | 2/2014 | Alon et al. |
| 8,652,203 B2 | 2/2014 | Quadri et al. |
| 8,668,733 B2 | 3/2014 | Haug et al. |
| 8,679,174 B2 | 3/2014 | Ottma et al. |
| 8,679,404 B2 | 3/2014 | Liburd et al. |
| 8,685,086 B2 | 4/2014 | Navia et al. |
| 8,721,708 B2 | 5/2014 | Sèguin et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,758,432 B2 | 6/2014 | Solem |
| 8,764,818 B2 | 7/2014 | Gregg |
| 8,771,344 B2 | 7/2014 | Tran et al. |
| 8,778,020 B2 | 7/2014 | Gregg et al. |
| 8,784,337 B2 | 7/2014 | Voeller et al. |
| 8,784,478 B2 | 7/2014 | Tuval et al. |
| 8,784,481 B2 | 7/2014 | Alkhatib et al. |

(56) References Cited

U.S. PATENT DOCUMENTS

| | | |
|---|---|---|
| 8,790,387 B2 | 7/2014 | Nguyen et al. |
| 8,795,357 B2 | 8/2014 | Yohanan et al. |
| 8,808,356 B2 | 8/2014 | Braido et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,858,620 B2 | 10/2014 | Salahieh et al. |
| 8,870,948 B1 | 10/2014 | Erzberger et al. |
| 8,870,950 B2 | 10/2014 | Hacohen |
| 8,876,893 B2 | 11/2014 | Dwork et al. |
| 8,911,455 B2 | 12/2014 | Quadri et al. |
| 8,926,693 B2 | 1/2015 | Duffy et al. |
| 8,926,694 B2 | 1/2015 | Costello |
| 8,939,960 B2 | 1/2015 | Rosenman et al. |
| 8,945,209 B2 | 2/2015 | Bonyuet et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |
| 8,986,375 B2 | 3/2015 | Garde et al. |
| 8,998,980 B2 | 4/2015 | Shipley et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,028,545 B2 | 5/2015 | Taylor |
| 9,034,032 B2 | 5/2015 | McLean et al. |
| 9,055,937 B2 | 6/2015 | Rowe et al. |
| 9,066,801 B2 | 6/2015 | Kovalsky et al. |
| 9,078,749 B2 | 7/2015 | Lutter et al. |
| 9,078,751 B2 | 7/2015 | Naor |
| 9,125,738 B2 | 9/2015 | Figulla et al. |
| 9,173,737 B2 | 11/2015 | Hill et al. |
| 9,180,004 B2 | 11/2015 | Alkhatib |
| 9,186,249 B2 | 11/2015 | Rolando et al. |
| 9,277,990 B2 | 3/2016 | Klima et al. |
| 9,277,993 B2 | 3/2016 | Gamarra et al. |
| 9,289,291 B2 | 3/2016 | Gorman et al. |
| 9,295,551 B2 | 3/2016 | Straubinger et al. |
| 9,445,897 B2 | 9/2016 | Bishop et al. |
| 9,456,877 B2 | 10/2016 | Weitzner et al. |
| 9,681,968 B2 | 6/2017 | Goetz et al. |
| 9,687,345 B2 | 6/2017 | Rabito et al. |
| 9,700,329 B2 | 7/2017 | Metzger et al. |
| 9,700,411 B2 | 7/2017 | Klima et al. |
| 9,724,083 B2 | 8/2017 | Quadri et al. |
| 9,730,790 B2 | 8/2017 | Quadri et al. |
| 9,730,791 B2 | 8/2017 | Ratz et al. |
| 9,795,479 B2 | 10/2017 | Lim et al. |
| 9,833,313 B2 | 12/2017 | Board et al. |
| 9,861,473 B2 | 1/2018 | Lafontaine |
| 9,861,476 B2 | 1/2018 | Salahieh et al. |
| 9,861,477 B2 | 1/2018 | Backus et al. |
| 9,867,698 B2 | 1/2018 | Kovalsky et al. |
| 9,877,830 B2 | 1/2018 | Lim et al. |
| 9,889,029 B2 | 2/2018 | Li et al. |
| 9,895,225 B2 | 2/2018 | Rolando et al. |
| 9,925,045 B2 | 3/2018 | Creaven et al. |
| 10,004,599 B2 | 6/2018 | Rabito et al. |
| 10,117,744 B2 | 11/2018 | Ratz et al. |
| 10,179,044 B2 | 1/2019 | Ratz et al. |
| 10,219,897 B2 | 3/2019 | Essinger et al. |
| 10,350,065 B2 | 7/2019 | Quadri |
| 10,350,066 B2 | 7/2019 | Cooper et al. |
| 10,376,363 B2 | 8/2019 | Quadri et al. |
| 10,555,809 B2 | 2/2020 | Hastings et al. |
| 10,575,951 B2 | 3/2020 | Johnson et al. |
| 10,583,000 B2 | 3/2020 | Ratz et al. |
| 10,639,146 B2 | 5/2020 | Quadri et al. |
| 10,695,177 B2 | 6/2020 | Hariton et al. |
| 10,758,344 B2 | 9/2020 | Hariton et al. |
| 11,406,499 B2 | 8/2022 | Zhang et al. |
| 11,452,598 B2 | 9/2022 | Essinger et al. |
| 11,672,658 B2 | 6/2023 | Hariton et al. |
| 11,701,225 B2 | 7/2023 | Hammer et al. |
| 11,903,829 B1 | 2/2024 | Ma et al. |
| 2001/0021872 A1 | 9/2001 | Bailey et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2002/0173842 A1 | 11/2002 | Buchanan |
| 2003/0050694 A1 | 3/2003 | Yang et al. |
| 2003/0100939 A1 | 5/2003 | Yodfat et al. |
| 2003/0105517 A1 | 6/2003 | White et al. |
| 2003/0120333 A1 | 6/2003 | Ouriel et al. |
| 2003/0130729 A1 | 7/2003 | Paniagua et al. |
| 2003/0158597 A1 | 8/2003 | Quiachon et al. |
| 2003/0176914 A1 | 9/2003 | Rabkin et al. |
| 2003/0199971 A1 | 10/2003 | Tower et al. |
| 2003/0212454 A1 | 11/2003 | Scott et al. |
| 2003/0220683 A1 | 11/2003 | Minasian et al. |
| 2004/0039436 A1 | 2/2004 | Spenser et al. |
| 2004/0092858 A1 | 5/2004 | Wilson et al. |
| 2004/0117009 A1 | 6/2004 | Cali et al. |
| 2004/0133263 A1 | 7/2004 | Dusbabek et al. |
| 2004/0133273 A1 | 7/2004 | Cox |
| 2004/0186563 A1 | 9/2004 | Lobbi |
| 2004/0186565 A1 | 9/2004 | Schreck |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2004/0260389 A1 | 12/2004 | Case et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137691 A1 | 6/2005 | Salahieh et al. |
| 2005/0137698 A1 | 6/2005 | Salahieh et al. |
| 2005/0159811 A1 | 7/2005 | Lane |
| 2005/0182486 A1 | 8/2005 | Gabbay |
| 2005/0203614 A1 | 9/2005 | Forster et al. |
| 2005/0203617 A1 | 9/2005 | Forster et al. |
| 2005/0216079 A1 | 9/2005 | MaCoviak |
| 2005/0234546 A1 | 10/2005 | Nugent et al. |
| 2005/0288766 A1 | 12/2005 | Plain et al. |
| 2006/0020327 A1 | 1/2006 | Lashinski et al. |
| 2006/0025857 A1 | 2/2006 | Bergheim et al. |
| 2006/0058872 A1 | 3/2006 | Salahieh et al. |
| 2006/0095115 A1 | 5/2006 | Bladillah et al. |
| 2006/0142837 A1 | 6/2006 | Haverkost et al. |
| 2006/0149350 A1 | 7/2006 | Patel et al. |
| 2006/0161249 A1 | 7/2006 | Realyvasquez et al. |
| 2006/0173537 A1 | 8/2006 | Yang et al. |
| 2006/0195134 A1 | 8/2006 | Crittenden |
| 2006/0195183 A1 | 8/2006 | Navia et al. |
| 2006/0212110 A1 | 9/2006 | Osborne et al. |
| 2006/0229719 A1 | 10/2006 | Marquez et al. |
| 2006/0241745 A1 | 10/2006 | Solem |
| 2006/0259135 A1 | 11/2006 | Navia et al. |
| 2006/0259137 A1 | 11/2006 | Artof et al. |
| 2006/0276874 A1 | 12/2006 | Wilson et al. |
| 2006/0293745 A1 | 12/2006 | Carpentier et al. |
| 2007/0005131 A1 | 1/2007 | Taylor |
| 2007/0010877 A1 | 1/2007 | Salahieh et al. |
| 2007/0027534 A1 | 2/2007 | Bergheim et al. |
| 2007/0043435 A1 | 2/2007 | Seguin et al. |
| 2007/0050021 A1 | 3/2007 | Johnson |
| 2007/0066863 A1 | 3/2007 | Rafiee et al. |
| 2007/0088431 A1 | 4/2007 | Bourang et al. |
| 2007/0100432 A1 | 5/2007 | Case et al. |
| 2007/0100439 A1 | 5/2007 | Cangialosi et al. |
| 2007/0112422 A1 | 5/2007 | Dehdashtian |
| 2007/0129794 A1 | 6/2007 | Realyvasquez |
| 2007/0142906 A1 | 6/2007 | Figulla et al. |
| 2007/0156224 A1 | 7/2007 | Cioanta et al. |
| 2007/0203503 A1 | 8/2007 | Salahieh et al. |
| 2007/0203575 A1 | 8/2007 | Forster et al. |
| 2007/0213813 A1 | 9/2007 | Von Segesser et al. |

(56) References Cited

U.S. PATENT DOCUMENTS

| | | |
|---|---|---|
| 2007/0255394 A1 | 11/2007 | Ryan |
| 2007/0270943 A1 | 11/2007 | Solem et al. |
| 2008/0021546 A1 | 1/2008 | Patz et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0097581 A1 | 4/2008 | Shanley |
| 2008/0114442 A1 | 5/2008 | Mitchell et al. |
| 2008/0125853 A1 | 5/2008 | Bailey et al. |
| 2008/0147179 A1 | 6/2008 | Cai et al. |
| 2008/0147183 A1 | 6/2008 | Styrc |
| 2008/0154355 A1 | 6/2008 | Benichou et al. |
| 2008/0161910 A1 | 7/2008 | Revuelta et al. |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0228254 A1 | 9/2008 | Ryan |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2009/0005863 A1 | 1/2009 | Goetz et al. |
| 2009/0054968 A1 | 2/2009 | Bonhoeffer et al. |
| 2009/0054974 A1 | 2/2009 | McGuckin et al. |
| 2009/0076598 A1 | 3/2009 | Salahieh et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0216310 A1 | 8/2009 | Straubinger et al. |
| 2009/0216313 A1 | 8/2009 | Straubinger et al. |
| 2009/0216322 A1 | 8/2009 | Le et al. |
| 2009/0222076 A1 | 9/2009 | Figulla et al. |
| 2009/0234443 A1 | 9/2009 | Ottma et al. |
| 2009/0240320 A1 | 9/2009 | Tuval et al. |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2009/0306768 A1 | 12/2009 | Quadri |
| 2009/0319037 A1 | 12/2009 | Rowe et al. |
| 2010/0016958 A1 | 1/2010 | St. Goar et al. |
| 2010/0024818 A1 | 2/2010 | Stenzler et al. |
| 2010/0049313 A1 | 2/2010 | Alon et al. |
| 2010/0069852 A1 | 3/2010 | Kelley |
| 2010/0114305 A1 | 5/2010 | Kang et al. |
| 2010/0131054 A1 | 5/2010 | Tuval et al. |
| 2010/0137979 A1 | 6/2010 | Tuval et al. |
| 2010/0174362 A1 | 7/2010 | Straubinger et al. |
| 2010/0191326 A1 | 7/2010 | Alkhatib |
| 2010/0204781 A1 | 8/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0262231 A1 | 10/2010 | Tuval et al. |
| 2010/0305685 A1 | 12/2010 | Millwee et al. |
| 2010/0312333 A1 | 12/2010 | Navia et al. |
| 2011/0015616 A1 | 1/2011 | Straubinger et al. |
| 2011/0015729 A1 | 1/2011 | Jimenez et al. |
| 2011/0137397 A1 | 6/2011 | Chau et al. |
| 2011/0178597 A9 | 7/2011 | Navia et al. |
| 2011/0208290 A1 | 8/2011 | Straubinger et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0238159 A1 | 9/2011 | Guyenot et al. |
| 2011/0264196 A1 | 10/2011 | Savage et al. |
| 2011/0264198 A1 | 10/2011 | Murray et al. |
| 2011/0288634 A1 | 11/2011 | Tuval et al. |
| 2011/0313515 A1 | 12/2011 | Quadri et al. |
| 2011/0319989 A1 | 12/2011 | Lane et al. |
| 2012/0022639 A1 | 1/2012 | Hacohen et al. |
| 2012/0035722 A1 | 2/2012 | Tuval |
| 2012/0041550 A1 | 2/2012 | Salahieh et al. |
| 2012/0046741 A1 | 2/2012 | Tuval et al. |
| 2012/0046742 A1 | 2/2012 | Tuval et al. |
| 2012/0078360 A1 | 3/2012 | Rafiee |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0185039 A1 | 7/2012 | Tuval et al. |
| 2012/0197386 A1 | 8/2012 | Von Segesser et al. |
| 2012/0209374 A1 | 8/2012 | Bonhoeffer et al. |
| 2012/0215303 A1 | 8/2012 | Quadri et al. |
| 2012/0271398 A1 | 10/2012 | Essinger et al. |
| 2012/0283823 A1 | 11/2012 | Bonhoeffer et al. |
| 2012/0290062 A1 | 11/2012 | McNamara et al. |
| 2012/0296418 A1 | 11/2012 | Bonyuet et al. |
| 2012/0310328 A1 | 12/2012 | Olson et al. |
| 2012/0310336 A1 | 12/2012 | Figulla et al. |
| 2013/0006294 A1 | 1/2013 | Kashkarov et al. |
| 2013/0035759 A1 | 2/2013 | Gross et al. |
| 2013/0073035 A1 | 3/2013 | Tuval et al. |
| 2013/0079869 A1 | 3/2013 | Straubinger et al. |
| 2013/0190861 A1 | 7/2013 | Chau et al. |
| 2013/0190862 A1 | 7/2013 | Pintor et al. |
| 2013/0197622 A1 | 8/2013 | Mitra et al. |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0274595 A1* | 10/2013 | Kermode ......... A61B 17/12172 |
| | | 600/585 |
| 2013/0310928 A1 | 11/2013 | Morriss et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0100651 A1 | 4/2014 | Kheradvar et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214157 A1 | 7/2014 | Börtlein et al. |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0222144 A1 | 8/2014 | Eberhardt et al. |
| 2014/0243966 A1 | 8/2014 | Garde et al. |
| 2014/0257467 A1 | 9/2014 | Lane et al. |
| 2014/0277390 A1 | 9/2014 | Ratz et al. |
| 2014/0277403 A1 | 9/2014 | Peter |
| 2014/0277412 A1 | 9/2014 | Börtlein et al. |
| 2014/0277422 A1 | 9/2014 | Ratz et al. |
| 2014/0277426 A1 | 9/2014 | Dakin et al. |
| 2014/0277427 A1 | 9/2014 | Ratz et al. |
| 2014/0296624 A1* | 10/2014 | Kermode ............ A61M 60/47 |
| | | 600/37 |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |

(56) References Cited

U.S. PATENT DOCUMENTS

| | | |
|---|---|---|
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0364939 A1 | 12/2014 | Deshmukh et al. |
| 2014/0364941 A1* | 12/2014 | Edmiston ......... A61B 17/12177 623/2.11 |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371847 A1 | 12/2014 | Madrid et al. |
| 2014/0371848 A1 | 12/2014 | Murray et al. |
| 2015/0005863 A1 | 1/2015 | Para |
| 2015/0018944 A1 | 1/2015 | O'Connell et al. |
| 2015/0039083 A1 | 2/2015 | Rafiee |
| 2015/0142103 A1 | 5/2015 | Vidlund |
| 2015/0148731 A1 | 5/2015 | Mcnamara et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0272737 A1 | 10/2015 | Dale et al. |
| 2015/0297346 A1 | 10/2015 | Duffy et al. |
| 2015/0335429 A1 | 11/2015 | Morriss et al. |
| 2015/0351903 A1 | 12/2015 | Morriss et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113768 A1 | 4/2016 | Ganesan et al. |
| 2016/0143732 A1 | 5/2016 | Glimsdale |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0213473 A1 | 7/2016 | Hacohen et al. |
| 2016/0235529 A1 | 8/2016 | Ma et al. |
| 2016/0278923 A1 | 9/2016 | Krans et al. |
| 2016/0279386 A1 | 9/2016 | Dale et al. |
| 2016/0310267 A1 | 10/2016 | Zeng et al. |
| 2017/0079785 A1 | 3/2017 | Li |
| 2017/0128209 A1 | 5/2017 | Morriss et al. |
| 2017/0216023 A1 | 8/2017 | Lane et al. |
| 2017/0216575 A1 | 8/2017 | Asleson et al. |
| 2017/0257902 A1 | 9/2017 | Xing et al. |
| 2017/0258614 A1 | 9/2017 | Griffin |
| 2017/0325945 A1 | 11/2017 | Dale et al. |
| 2017/0325954 A1 | 11/2017 | Perszyk |
| 2017/0333186 A1 | 11/2017 | Spargias |
| 2017/0348096 A1 | 12/2017 | Anderson |
| 2017/0367821 A1 | 12/2017 | Landon et al. |
| 2017/0367823 A1 | 12/2017 | Hariton et al. |
| 2018/0014931 A1 | 1/2018 | Morriss et al. |
| 2018/0021129 A1 | 1/2018 | Peterson et al. |
| 2018/0055629 A1 | 3/2018 | Oba et al. |
| 2018/0055636 A1 | 3/2018 | Valencia et al. |
| 2018/0085218 A1 | 3/2018 | Eidenschink |
| 2018/0110534 A1 | 4/2018 | Gavala et al. |
| 2018/0116790 A1 | 5/2018 | Ratz et al. |
| 2018/0214664 A1 | 8/2018 | Kim et al. |
| 2018/0344490 A1 | 12/2018 | Fox et al. |
| 2019/0008639 A1 | 1/2019 | Landon et al. |
| 2019/0008640 A1 | 1/2019 | Cooper et al. |
| 2019/0060072 A1 | 2/2019 | Zeng |
| 2019/0262129 A1 | 8/2019 | Cooper et al. |
| 2020/0000579 A1 | 1/2020 | Manash et al. |
| 2020/0108225 A1 | 4/2020 | Jamal et al. |
| 2020/0138572 A1 | 5/2020 | Zhao et al. |
| 2020/0323668 A1 | 10/2020 | Diedering et al. |
| 2020/0345494 A1 | 11/2020 | Srinimukesh et al. |
| 2020/0352718 A1 | 11/2020 | Rowe et al. |
| 2021/0145576 A1 | 5/2021 | Becerra et al. |
| 2021/0259835 A1 | 8/2021 | Tyler, II et al. |
| 2021/0307900 A1 | 10/2021 | Hacohen |
| 2021/0378817 A1 | 12/2021 | Nia et al. |
| 2021/0386544 A1 | 12/2021 | Cooper et al. |
| 2022/0142777 A1 | 5/2022 | Scheinblum et al. |
| 2022/0287836 A1 | 9/2022 | Landon et al. |
| 2022/0346993 A1 | 11/2022 | Srinimukesh et al. |
| 2023/0000624 A1 | 1/2023 | Okabe et al. |
| 2023/0200980 A1 | 6/2023 | Peterson et al. |
| 2023/0218391 A1 | 7/2023 | Dass et al. |
| 2023/0380963 A1 | 11/2023 | Kaufman et al. |
| 2023/0390052 A1 | 12/2023 | Okafor et al. |
| 2023/0404753 A1 | 12/2023 | Luong et al. |
| 2024/0008978 A1 | 1/2024 | Nawalakhe et al. |
| 2024/0091000 A1 | 3/2024 | King et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 10010074 B4 | 4/2005 |
| DE | 102006052564 B3 | 12/2007 |
| EP | 0144167 A2 | 6/1985 |
| EP | 0103546 B1 | 5/1988 |
| EP | 0592410 B1 | 10/1995 |
| EP | 0850607 A1 | 7/1998 |
| EP | 0597967 B1 | 12/1999 |
| EP | 1057460 A1 | 12/2000 |
| EP | 1088529 A2 | 4/2001 |
| EP | 1469797 A1 | 10/2004 |
| EP | 1259194 B1 | 2/2005 |
| EP | 1171059 B1 | 11/2005 |
| EP | 1255510 B1 | 4/2007 |
| EP | 1239901 B1 | 10/2007 |
| EP | 1849440 A1 | 10/2007 |
| EP | 1570809 B1 | 1/2009 |
| EP | 1472996 B1 | 9/2009 |
| EP | 1653888 B1 | 9/2009 |
| EP | 1935377 B1 | 3/2010 |
| EP | 1369098 B1 | 4/2014 |
| EP | 2124826 B1 | 7/2014 |
| EP | 2745805 B1 | 6/2015 |
| EP | 2749254 B1 | 6/2015 |
| EP | 2918249 A2 | 9/2015 |
| EP | 2168536 B1 | 4/2016 |
| EP | 2413842 B1 | 8/2017 |
| EP | 2446915 B1 | 1/2018 |
| EP | 3057541 B1 | 1/2018 |
| EP | 3037064 B1 | 3/2018 |
| EP | 3046511 B1 | 3/2018 |
| EP | 3142603 B1 | 3/2018 |
| EP | 3075354 B1 | 11/2018 |
| EP | 3184083 B1 | 2/2019 |
| EP | 3417813 B1 | 5/2020 |
| EP | 2777616 B1 | 8/2020 |
| EP | 3139864 B1 | 11/2020 |
| EP | 2750630 B1 | 6/2021 |
| EP | 2777617 B1 | 9/2022 |
| EP | 2948103 B1 | 12/2022 |
| EP | 2967858 B1 | 1/2023 |
| EP | 3570779 B1 | 2/2023 |
| EP | 3294220 B1 | 12/2023 |
| FR | 2788217 A1 | 7/2000 |
| GB | 1264471 A | 2/1972 |
| GB | 1315844 A | 5/1973 |

(56) References Cited

FOREIGN PATENT DOCUMENTS

| | | |
|---|---|---|
| GB | 2056023 A | 3/1981 |
| GB | 2398245 A | 8/2004 |
| SU | 1271508 A1 | 11/1986 |
| WO | 1991016041 A1 | 10/1991 |
| WO | 1991017720 A1 | 11/1991 |
| WO | 1992017118 A1 | 10/1992 |
| WO | 1993001768 A1 | 2/1993 |
| WO | 1997024080 A1 | 7/1997 |
| WO | 1998029057 A1 | 7/1998 |
| WO | 1999033414 A1 | 7/1999 |
| WO | 1999040964 A1 | 8/1999 |
| WO | 1999047075 A1 | 9/1999 |
| WO | 2000018333 A1 | 4/2000 |
| WO | 2000041652 A1 | 7/2000 |
| WO | 2000047139 A1 | 8/2000 |
| WO | 2000061034 A1 | 10/2000 |
| WO | 2001028459 A1 | 4/2001 |
| WO | 2001035878 A2 | 5/2001 |
| WO | 2001049213 A2 | 7/2001 |
| WO | 2001054624 A1 | 8/2001 |
| WO | 2001054625 A1 | 8/2001 |
| WO | 2001062189 A1 | 8/2001 |
| WO | 2001064137 A1 | 9/2001 |
| WO | 2001076510 A2 | 10/2001 |
| WO | 2002036048 A1 | 5/2002 |
| WO | 2003047468 A1 | 6/2003 |
| WO | 2003092554 A1 | 11/2003 |
| WO | 2004030569 A2 | 4/2004 |
| WO | 2005011534 A1 | 2/2005 |
| WO | 2005034812 A1 | 4/2005 |
| WO | 2005087140 A1 | 9/2005 |
| WO | 2005102015 A2 | 11/2005 |
| WO | 2006014233 A2 | 2/2006 |
| WO | 2006034008 A2 | 3/2006 |
| WO | 2006085225 A1 | 8/2006 |
| WO | 2006108090 A2 | 10/2006 |
| WO | 2006111391 A1 | 10/2006 |
| WO | 2006138173 A2 | 12/2006 |
| WO | 2007025028 A1 | 3/2007 |
| WO | 2008005405 A2 | 1/2008 |
| WO | 2008035337 A2 | 3/2008 |
| WO | 2008125153 A1 | 10/2008 |
| WO | 2008147964 A1 | 12/2008 |
| WO | 2008150529 A1 | 12/2008 |
| WO | 2009024859 A2 | 2/2009 |
| WO | 2009026563 A2 | 2/2009 |
| WO | 2009042196 A2 | 4/2009 |
| WO | 2009091509 A1 | 7/2009 |
| WO | 2009094500 A1 | 7/2009 |
| WO | 2010005524 A2 | 1/2010 |
| WO | 2010008549 A1 | 1/2010 |
| WO | 2010121076 A2 | 10/2010 |
| WO | 2011002996 A2 | 1/2011 |
| WO | 2011081997 A1 | 7/2011 |
| WO | 2012032187 A1 | 3/2012 |
| WO | 2012095455 A2 | 7/2012 |
| WO | 2013028387 A2 | 2/2013 |
| WO | 2013106585 A1 | 7/2013 |
| WO | 2014018432 A2 | 1/2014 |
| WO | 2014079291 A1 | 5/2014 |
| WO | 2014145338 A1 | 9/2014 |
| WO | 2014149865 A1 | 9/2014 |
| WO | 2014163706 A1 | 10/2014 |
| WO | 2014194178 A1 | 12/2014 |
| WO | 2015057407 A1 | 4/2015 |
| WO | 2015077274 A1 | 5/2015 |
| WO | 2016016899 A1 | 2/2016 |
| WO | 2017035487 A1 | 3/2017 |
| WO | 2018213209 A1 | 11/2018 |
| WO | 2022002054 A1 | 1/2022 |
| WO | 2023006048 A1 | 2/2023 |
| WO | 2023076103 A1 | 5/2023 |
| WO | 2023081236 A1 | 5/2023 |
| WO | 2023091769 A1 | 5/2023 |
| WO | 2023096804 A1 | 6/2023 |
| WO | 2023154250 A1 | 8/2023 |
| WO | 2023196150 A1 | 10/2023 |
| WO | 2023244454 A1 | 12/2023 |
| WO | 2023244767 A1 | 12/2023 |
| WO | 2023250114 A1 | 12/2023 |
| WO | 2024001789 A1 | 1/2024 |
| WO | 2024003620 A1 | 1/2024 |
| WO | 2024007575 A1 | 1/2024 |
| WO | 2024009540 A1 | 1/2024 |
| WO | 2024010739 A1 | 1/2024 |
| WO | 2024030520 A1 | 2/2024 |

OTHER PUBLICATIONS

Andersen, Henning Rud, "History of Percutaneous Aortic Valve Prosthesis," Herz 34 2009 Nr. 5, Urban&Vogel, pp. 343-346, Skejby University Hospital Department of Cardiology, Aarhus, Denmark.
Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.
Inoue, M.D., Kanji, et al., "Clinical Application of Transvenous Mitral Commissurotomy by a New Balloon Catheter," The Journal of Thoracic and Cardiovascular Surgery 87:394-402, 1984.
Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Rashkind, M.D., William J., "Historical Aspects of Interventional Cardiology: Past, Present, Future," Texas Heart Institute Journal, Interventional Cardiology, pp. 363-367.
Rösch, M.D., Josef, "The Birth, Early Years and Future of Interventional Radiology," J Vasc Interv Radiol 2003; 14:841-853.
Ross, F.R.C.S., D.N., "Aortic Valve Surgery," Guy's Hospital, London, pp. 192-197, approximately 1968.
Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.
Wheatley, M.D., David J., "Valve Prostheses," Rob&Smith's Operative Surgery, Fourth Edition, pp. 415-424, Butterworths 1986.
Bavaria, Joseph E. M.D. et al.: "Transcatheter Mitral Valve Implantation: The Future Gold Standard for MR?".
Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409.
Bavaria, Joseph E. M.D.: "CardiAQ Valve Technologies: Transcatheter Mitral Valve Implantation," Sep. 21, 2009.
Berreklouw, Eric, PhD, et al., "Sutureless Mitral Valve Replacement With Bioprostheses and Nitinol Attachment Rings: Feasibility In Acute Pig Experiments," The Journal of Thoracic and Cardiovascular Surgery, vol. 142, No. 2, Aug. 2011 in 7 pages.
Boudjemline, Younes, et al., "Steps Toward the Percutaneous Replacement of Atrioventricular Valves," JACC, vol. 46, No. 2, Jul. 19, 2005:360-5.
CardiAQ Valve Technologies, "Innovations in Heart Valve Therapy," In3 San Francisco, Jun. 18, 2008, PowerPoint presentation in 19 slides.
Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.
Condado, Jose Antonio, et al., "Percutaneous Treatment of Heart Valves," Rev Esp Cardio. 2006;59(12):1225-31.
Feldman, Ted, MD. "Prospects for Percutaneous Valve Therapies," Circulation 2007;116:2866-2877.
Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA.
Fornell, Dave, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.

(56) References Cited

OTHER PUBLICATIONS

Grube, E. et al., "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.
Karimi, Houshang, et al., "Percutaneous Valve Therapies," SIS 2007 Yearbook, Chapter 11, pp. 1-11.
Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.
Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages.
Lutter, Georg, et al., "Off-Pump Transapical Mitral Valve Replacement," European Journal of Cardio-thoracic Surgery 36 (2009) 124-128.
Ma, Liang, et al., "'Double-Crowned Valved Stents For Off-Pump Mitral Valve Replacement," European Journal of Cardio-thoracic Surgery 28 (2005) 194-199.
Mack, Michael, M.D., "Antegrade Transcatheter Mitral valve Implantation: A Short-term Experience in Swine Model."
Mack, Michael, M.D., "Antegrade Transcatheter Mitral valve Implantation: On-Going Experience in Swine Model."
Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.
Preston-Maher, Georgia L., et al., "A Technical Review of Minimally Invasive Mitral Valve Replacements," Cardiovascular Engineering and Technology, vol. 6, No. 2, Jun. 2015, pp. 174-184.
Quadri, Arshad M.D., "Transcatheter Mitral Valve Implantation (TMVI) (An Acute In Vivo Study)."
Ratz, J. Brent, "LSI EMT Spotlight," May 15, 2009.
Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.
Ratz, J. Brent, "In3 Company Overview," Jun. 24, 2009.
Ruiz, Carlos E., "Overview of Novel Transcatheter Valve Technologies."
Spillner, J. et al., "New Sutureless 'Atrial-Mitral-Valve Prosthesis' For Minimally Invasive Mitral Valve Therapy," Textile Research Journal, 2010, in 7 pages.
Sondergaard, Lars, et al., "Transcatheter Mitral Valve Implantation: CardiAQ™," TCT 2013.
Sondergaard, Lars, et al., "Transcatheter Mitral Valve Implantation: CardiAQ™," EuroPCR 2013.
Sondergaard, Lars, "CardiAQ TMVR FIH—Generation 2," TVT symposium.
Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.
Webb, John G., et al., "Transcatheter Aortic Valve Implantation: The Evolution Of Prostheses, Delivery Systems And Approaches," Archives of Cardiovascular Disease (2012) 105, 153-159.
Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.
"CardiAQ Valve Technologies, Percutaneous Mitral Valve Replacement, Company Overview," at TVT on Jun. 25, 2009.
BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.
BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.
Neovasc corporate presentation, Oct. 2009, available at http://www.neovasc.com/investors/documents/Neovasc-Corporate-Presentation-October-2009.pdf.

\* cited by examiner

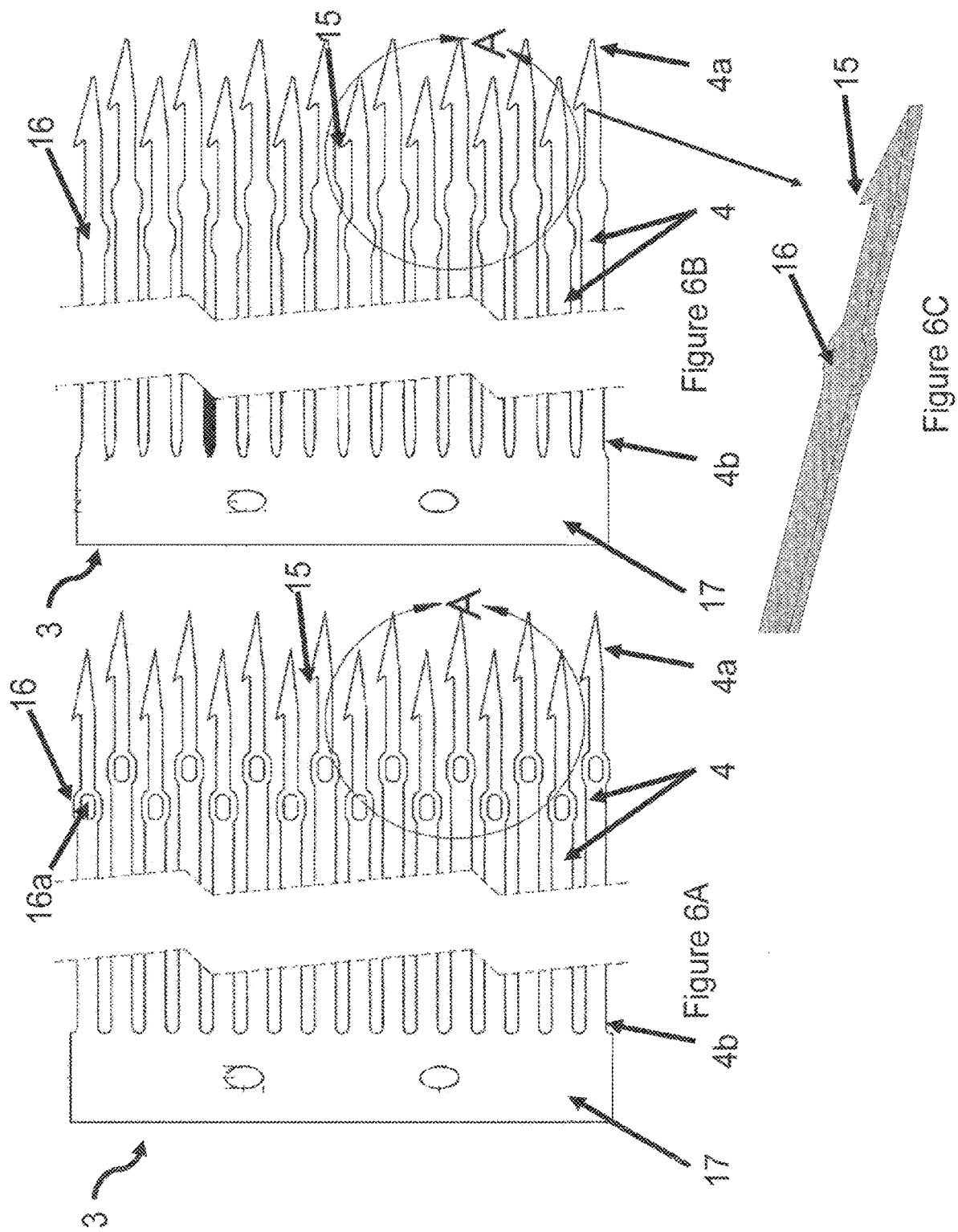

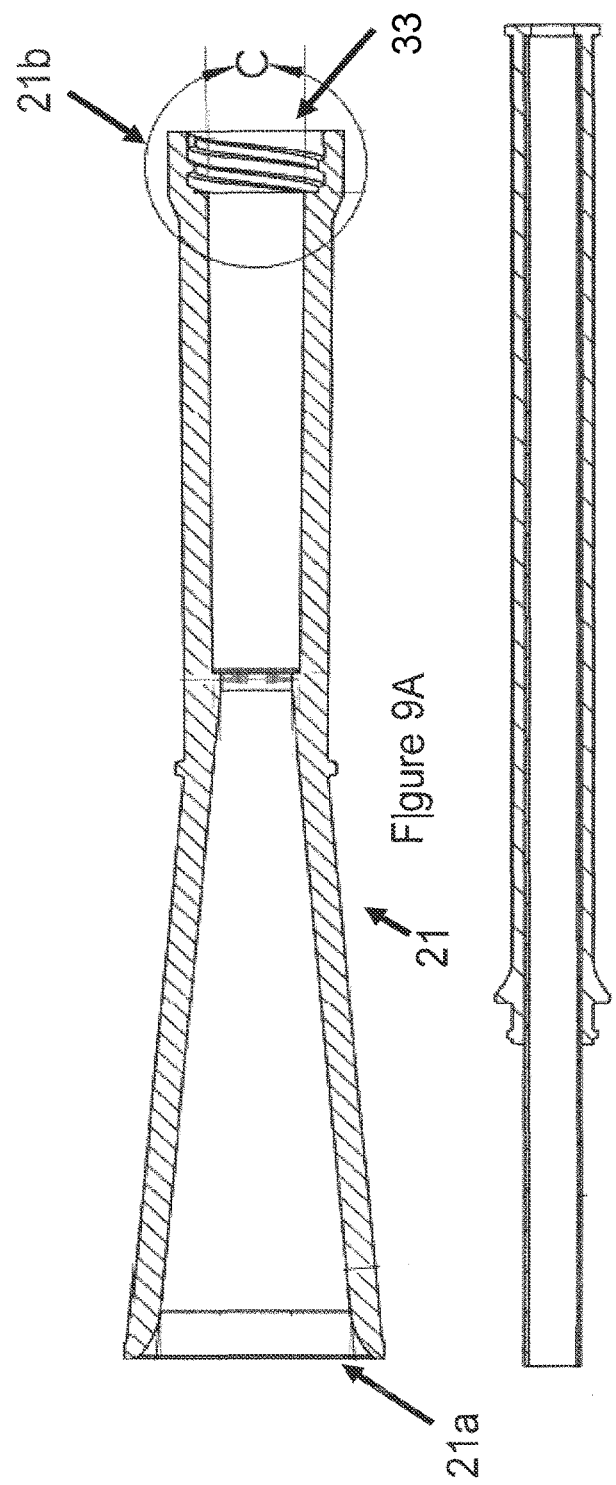
Figure 9A
Figure 9B
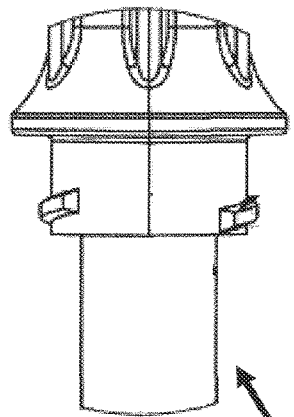
Figure 9C

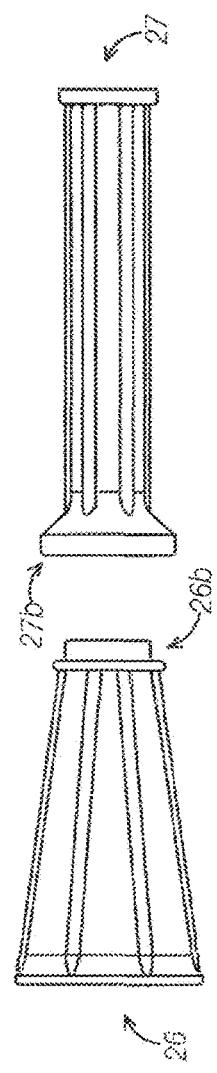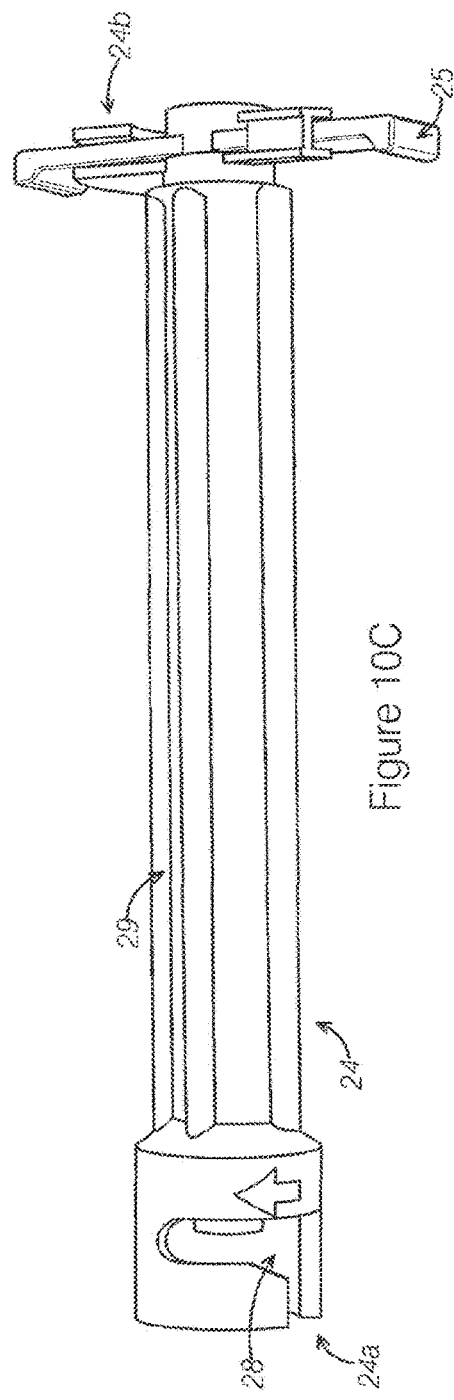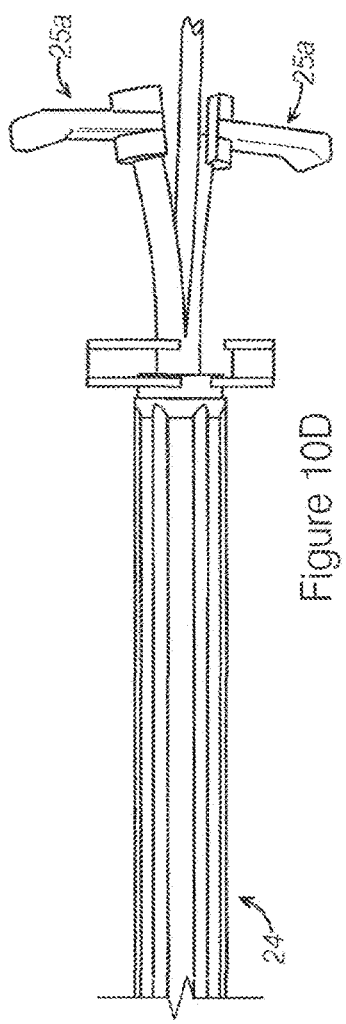
Figure 10A
Figure 10B
Figure 10C
Figure 10D

S100 — coupling the ventricular partitioning device to a delivery catheter

S110 — loading the ventricular partitioning device and a portion of the delivery catheter into a sleeve and creating a liquid-tight seal between a portion of the sleeve and the delivery catheter, wherein the delivery catheter or the sleeve includes a first fluid delivery port positioned thereon S120 — coupling a distal end of the sleeve to a guide catheter, wherein the guide catheter includes a second delivery port positioned thereon S130 — delivering fluid through at least one of the first fluid delivery port or the second fluid delivery port, wherein delivering the fluid creates a first pressure in the guide catheter that is greater than a second pressure in a ventricle

Figure 16

SYSTEMS AND METHODS FOR DELIVERING AN IMPLANTABLE DEVICE

CROSS REFERENCE TO RELATED APPLICATIONS

This application is a continuation of U.S. patent application Ser. No. 16/997,793, filed Aug. 19, 2020, which is a divisional application of U.S. patent application Ser. No. 15/559,680, filed Sep. 19, 2017, now U.S. Pat. No. 10,751,064, which was the National Stage of International Patent Application No. PCT/US2016/022863, filed Mar. 17, 2016, which claims the benefit of U.S. Provisional Application No. 62/136,248, filed Mar. 20, 2015, and titled "SYSTEMS AND METHODS FOR DELIVERING AN IMPLANTABLE DEVICE", the entire contents of each of which are herein incorporated by reference in their entireties.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

This invention relates to the field of ventricular devices useful for treating cardiac dysfunction.

BACKGROUND

Congestive heart failure (CHF) is a chronic medical condition in which the heart progressively enlarges. The enlarged heart cannot deliver sufficient oxygenated and nutrient rich blood to the body's cells, CHF is commonly associated with left ventricular dysfunction and/or diastolic dysfunction. Left ventricular dysfunction results from impaired emptying of the left ventricular heart chamber, in contrast, diastolic dysfunction refers to alterations in left ventricular properties that adversely affect ventricular filling and diastolic pressure.

A key aspect of normal diastolic filling is the contribution of left ventricular elastic recoil forces to left ventricular filling. Elastic recoil is the ability of the stretched heart to return to its resting position. For example, in a healthy heart, the end-diastolic dimension of the left ventricle may range from 36-56 mm (relaxed) and the end-systolic dimension of the left ventricle may range from 20-40 mm (contracted). A left ventricle in heart failure would typically have larger dimensions than those of a healthy heart. Elastic recoil forces are important in early diastole because they allow rapid and enhanced early filling by assisting the expansion of the left ventricle.

In the case of heart enlargement and/or a decrease in myocardial function, elastic recoil forces may be reduced or absent, thus ceasing to assist early ventricular filling and leading to an increase of the ventricular filling pressure. For example, a patient experiencing CHF typically has an ejection fraction of 40% or less.

Thus, there is a need for a new and useful system, device, and method for treating cardiac dysfunction. This invention provides such a new and useful system, device, and method.

SUMMARY

The present disclosure is directed to systems and methods for implantable device delivery. One aspect of the disclosure is directed to a delivery system for an implantable device. In some embodiments, a delivery system for an implantable device includes a delivery catheter including a tubular body having a proximal end and a distal end; a sleeve defining a lumen configured to receive the delivery catheter and the implantable device coupled thereto; a first fluid delivery port positioned on the delivery catheter or the sleeve; a mechanical seal coupled to the sleeve and configured to form a liquid-tight seal with the delivery catheter; and a guide catheter comprising a tubular body having a proximal end, a distal end, and a second fluid delivery port positioned thereon.

In some embodiments, the distal end of the delivery catheter is configured to couple to the implantable device. In some embodiments, the proximal end of the guide catheter is configured to be connected to a distal end of the sleeve. In some embodiments, the guide catheter includes a hemostatic valve positioned at the proximal end of the guide catheter.

In some embodiments, a first pressure in the guide catheter is greater than a second pressure in a ventricle when fluid is delivered through the guide catheter. In some embodiments, the system includes a pressurized fluid reservoir. In one embodiment, the pressurized fluid reservoir is configured to be in fluid communication with the delivery catheter. In some embodiments, the system includes a pump. In one embodiment, the pump is configured to deliver fluid through the delivery catheter.

In some embodiments, the mechanical seal is a gasket. In some embodiments, the implantable device is a ventricular partitioning device. In one embodiment, the implantable device includes a support frame including a plurality of radially expandable struts and a membrane coupled to the support frame. In one embodiment, the implantable device includes a foot for contacting a first interior wall portion of the ventricle.

In some embodiments, the first pressure in the guide catheter is about 200-600 mm Hg. In some embodiments, the second pressure in the ventricle is about 50-300 mm Hg.

In some embodiments, the fluid is delivered at a positive pressure into the first and/or second fluid delivery ports.

In some embodiments, the system includes a funnel. In one embodiment, the funnel includes a flared first end and a second end. In one embodiment, the flared first end is configured for receiving and collapsing the expandable device. In one embodiment, the second end of the funnel is coupleable to the sleeve.

One aspect of the disclosure is directed to methods of preparing a ventricular partitioning device for implantation. In some embodiments, a method of preparing a ventricular partitioning device for implantation using a delivery system includes coupling the ventricular partitioning device to a delivery catheter; loading the ventricular partitioning device and a portion of the delivery catheter into a sleeve and creating a liquid-tight seal between a portion of the sleeve and the delivery catheter; coupling a distal end of the sleeve to a guide catheter; and delivering fluid through the first fluid delivery port and/or the second fluid delivery port.

In some embodiments, the delivery catheter or the sleeve includes a first fluid delivery port positioned thereon. In some embodiments, the guide catheter includes a second fluid delivery port positioned thereon.

In some embodiments, the step of delivering the fluid creates a first pressure in the guide catheter that is greater than a second pressure in a ventricle.

In some embodiments, the method includes transferring the ventricular partitioning device from the sleeve to the guide catheter. In some embodiments, the method includes delivering the ventricular partitioning device from the guide catheter into the ventricle. In some embodiments, the method includes uncoupling the delivery catheter from the ventricular partitioning device.

In some embodiments, the method includes loading the ventricular partitioning device into a funnel device. In one embodiment, the funnel device includes a flared first end and a second end.

In one embodiment, the flared first end is configured for receiving and collapsing the expandable device.

In some embodiments, the sleeve is removably coupled to the second end of the funnel device. In one embodiment, the sleeve is configured for receiving the expandable device from the funnel device.

In some embodiments, the delivering fluid step includes delivering the fluid at a positive pressure. In some embodiments, the method includes maintaining the positive pressure in the guide catheter during delivery of the ventricular partitioning device into the ventricle.

In some embodiments, the first pressure in the guide catheter is about 200-600 mm Hg. In some embodiments, the second pressure in the ventricle is about 50-300 mm Hg.

In some embodiments, the method includes aspirating gas from the delivery system through the second fluid delivery port while fluid is delivered through the first fluid delivery port.

In some embodiments, the method includes removing bubbles from the delivery system using the first and/or second fluid delivery ports.

In some embodiments, the method includes allowing blood to exit the delivery system through the second fluid delivery port disposed on the guide catheter as the ventricular partitioning device is advanced from the sleeve into the guide catheter.

In some embodiments, delivering fluid through the first fluid delivery port and/or the second fluid delivery port includes delivering fluid through the first fluid delivery port into the guide catheter as the ventricular partitioning device is advanced through the guide catheter.

In some embodiments, the fluid is substantially maintained in the delivery system by the liquid-tight seal.

In some embodiments, the method includes sealing the second fluid delivery port disposed on the guide catheter at a time after the ventricular partitioning device has advanced distally beyond the second fluid delivery port.

In some embodiments, the delivering fluid step includes delivering the fluid using a pump at a flow rate between about 0.5 to 5 mL/second.

BRIEF DESCRIPTION OF THE DRAWINGS

FIGS. 6A-6C illustrate two embodiments of the struts of a ventricular partitioning device;

FIGS. 9A-9C illustrate a cross-sectional view of one embodiment of an implant loading system for a ventricular partitioning device;

FIGS. 10A-10D illustrates an alternative embodiment of an implant loading system for a ventricular partitioning device;

FIG. 16 provides a flow chart depicting one embodiment of a method of preparing a ventricular partitioning device for implantation using a delivery system.

DETAILED DESCRIPTION

Disclosed herein are systems and devices for treating cardiac dysfunction. In some instances, cardiac dysfunction may include diastolic dysfunction, mitral valve regurgitation, and/or heart failure.

In general, the systems and devices described herein may be used to treat a patient's heart suffering from heart failure. The systems and devices may be used to treat a patient's heart experiencing diastolic dysfunction or a condition exhibiting characteristics of diastolic dysfunction, and may involve implanting, within a ventricle of the heart, a device that partitions the ventricle into functional and nonfunctional portions. In some embodiments, the device may deform during systole and recoil during diastole to supplement the natural elastic recoil action of the ventricle. In some embodiments, the device may reduce the end-diastolic volume, end-diastolic pressure, and/or increase the ejection fraction.

Diastole represents the period of time in the heart cycle in which the ventricles are relaxed and not contracting. Throughout most of diastole, blood is passively flowing from the right and left atria into the right and left ventricles, respectively. As the ventricles begin to contract, the pressure in the ventricles exceeds that of the atria, and the mitral valve closes, ending diastole. At this time, the ventricular pressure and volume are referred to as end-diastolic pressure and end-diastolic volume, respectively.

Reduced ventricular compliance, for example due to an increased stiffness in the ventricular heart wall, may result in increased end-diastolic pressure and decreased end-diastolic volume. Diastolic dysfunction may also result from changes in left ventricle relaxation during diastole. For example, inotropic stimulation, fast heart rates, non-uniform heart activation, and altered timing of forces that oppose ventricular ejection may contribute to altered left ventricle relaxation.

Devices

Figure 1:
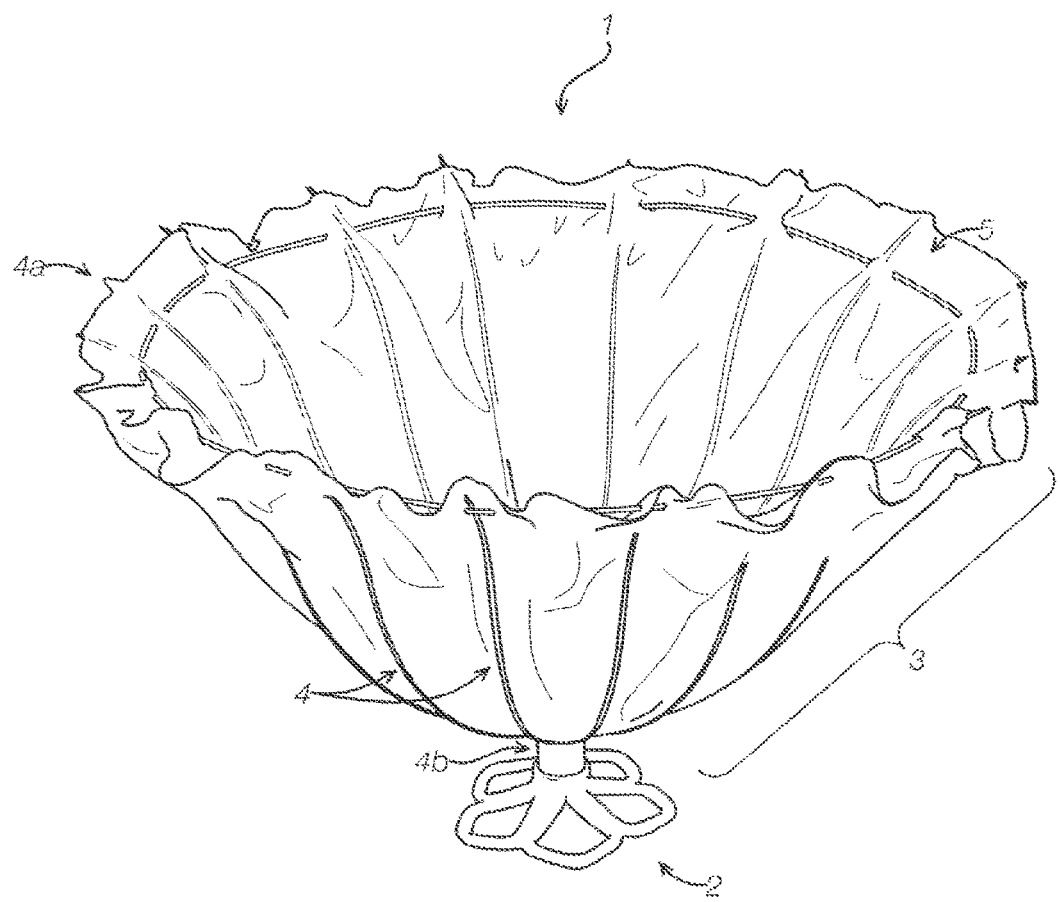
FIG. 1 illustrates one embodiment of a ventricular partitioning device.

FIG. 1 illustrates an expandable or implantable device, which may also be referred to as a ventricular partitioning device, 1 to treat cardiac dysfunction. In some embodiments, cardiac dysfunction may include diastolic dysfunction, mitral valve regurgitation, heart failure, and/or any other type of malady of the heart. The device may be delivered to the ventricle of a patient to treat cardiac dysfunction. In some embodiments, as shown in FIG. 1, a device for treating cardiac dysfunction may include a foot 2 for contacting a first interior wall portion of a heart. Further, in some embodiments, a device for treating cardiac dysfunction may include a support frame 3 including a plurality of radially expandable struts 4 and a membrane 5 coupled to the support frame 3. Each of the radially expandable struts 4 has a first free end 4a and a second end 4b coupled to the foot 2.

FIGS. 2A-2D and 3A-3C illustrate two embodiments of a foot 2 coupled to a stem 6 of an expandable device. The foot 2 of a ventricular partitioning device may contact an interior wall portion of a heart of a patient experiencing cardiac dysfunction. An interior wall portion of a heart may include an apex of a ventricle. In some embodiments, the foot 2 may contact the apex of the ventricle so that the entire device is underneath the papillary muscle located in the ventricle, such that the ventricular partitioning device does not interfere with the heart valve in the apex of the ventricle. In some embodiments, the foot 2 may contact the apex of the ventricle atraumatically such that the apex of the ventricle does not incur damage, trauma, and/or significant injury.

Figure 2A:
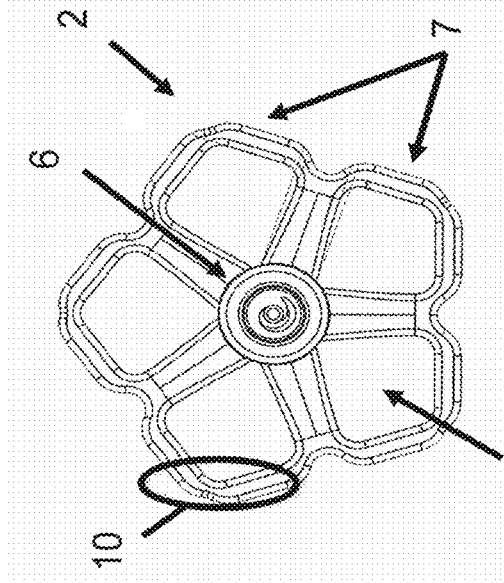
FIGS. 2A-2D illustrate one embodiment of a foot of a ventricular partitioning device.
Figure 3A:
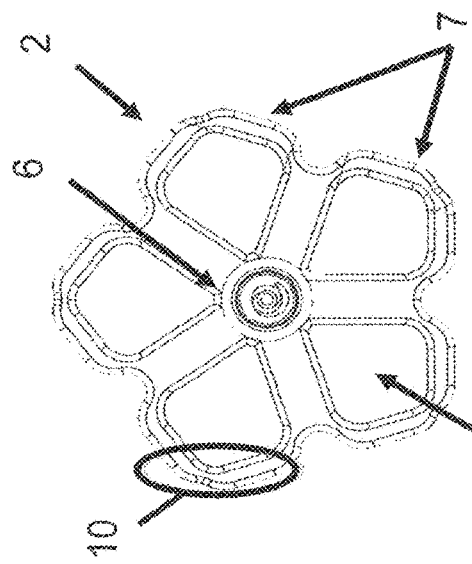
FIGS. 3A-3C illustrate an alternative embodiment of a foot of a ventricular partitioning device.
Figure 3B:
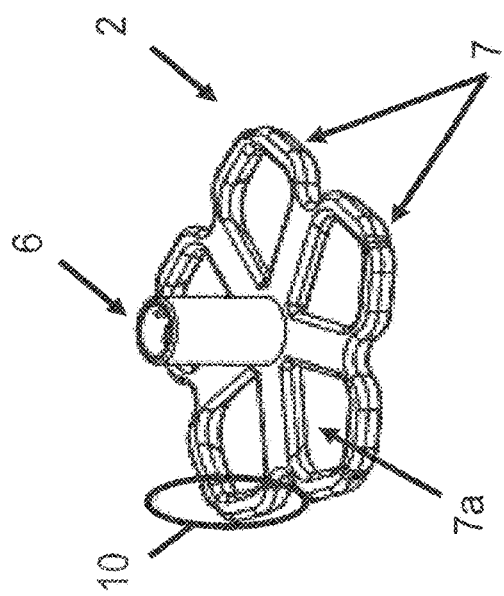
Figure 3C:
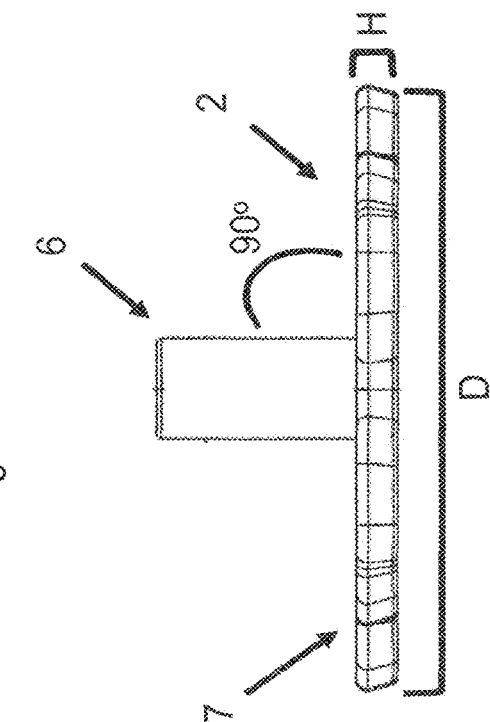

The foot 2 of the device, as shown in FIGS. 2A 3C, is supportive such that it does not collapse upon itself once implanted. However, the foot 2 may also be flexible, such that the device does not create focal pressure points (e.g., "hot spots") in the ventricle. To balance these properties of the ventricular partitioning device, the foot 2 of the ventricular partitioning device may include a thermoplastic elastomer. In some embodiments, the foot 2 may include thermoplastic silicone polyether polyurethane (TPU), such as DSM.

In some embodiments, as shown in FIGS. 2A-3C, the foot 2 may include a different material and/or durometer than the stem. In some embodiments, the foot 2 may include, Pursil TSPU, or any other thermoplastic material, such that the durometer is 70 A to 90 A and the flexural modulus or bending modulus is 15 MPa to 45 MPa. In one embodiment, the foot includes a durometer of 78 A to 84 A and a flexural modulus or bending modulus of 20 MPa to 40 MPa. In some embodiments, the stem 6 may include elasthane TPU, or any other thermoplastic material, such that the durometer is 45 D to 75 D and the flexural modulus or bending modulus is 100 MPa to 400 MPa. In one embodiment, the stem includes a durometer of 50 D to 70 D and a flexural modulus or bending modulus of 145 MPa to 390 MPa.

In some embodiments, the foot 2 of the ventricular partitioning device may include a radiopaque filler material to aid in visualization of the implant during and/or after implantation of the ventricular partitioning device in the heart of a patient. In some embodiments, the foot 2 may include 20% radiopaque filler. Alternatively, the foot 2 and stem 6 may include 40% radiopaque filler or any other percent of radiopaque filler suitable to the application. For example, the foot 2 and/or stem 6 may include between about 10 and 50% radiopaque filler, or at least about 10, 20, 30, or 40% radiopaque filler.

Figure 2B:
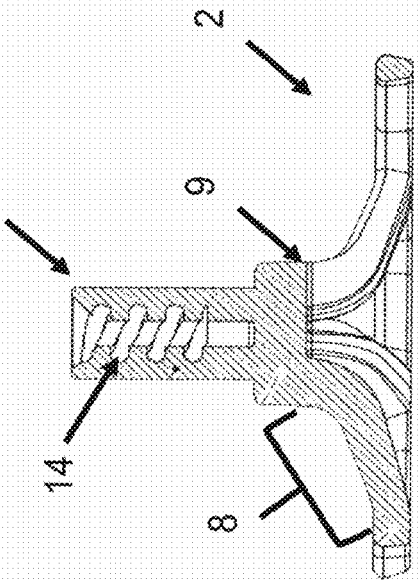
Figure 2C:
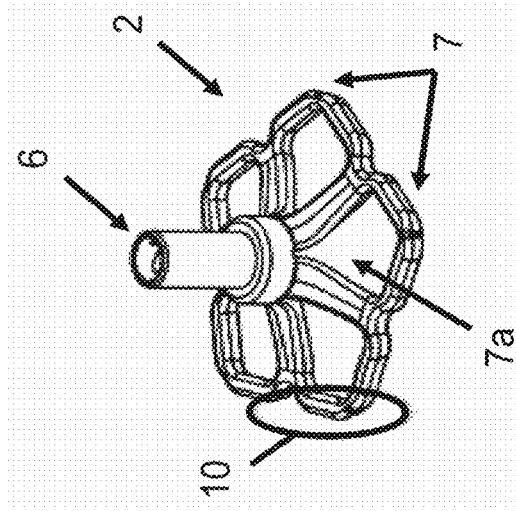

In some embodiments, as shown in FIGS. 2C and 3C, the foot 2 may have a height H ranging from 0.5 mm to 4.0 mm and a diameter D ranging from 13 mm to 17 mm, depending on the distance between the apex of the ventricle and the papillary muscle in the ventricle. In some embodiments, the foot 2 of the ventricular partitioning device may comprise a plurality of sections or petals 7. In some embodiments, a foot 2 may include 1, 2, 3, 4, 5, 6, 7, 8, 9, or 10 petals. In one embodiment, the foot 2 includes 5 petals, as shown in FIGS. 2A, 2B, 3A, and 3C. The petals 7 may include a looped configuration such that each petal includes an aperture 7a. Alternatively, the petals may comprise a solid configuration. Each petal 7 may be coupled to at least two other petals 7 of the foot 2 of the ventricular partitioning device. Alternatively, each petal 7 of the foot 2 may be separate and uncoupled from the other petals 7 of the foot 2. In some embodiments, the foot may alternatively include a screw for securing the ventricular partitioning device to the apex, a hub, or any other component suitable for positioning a ventricular partitioning device in a heart.

Figure 2D:
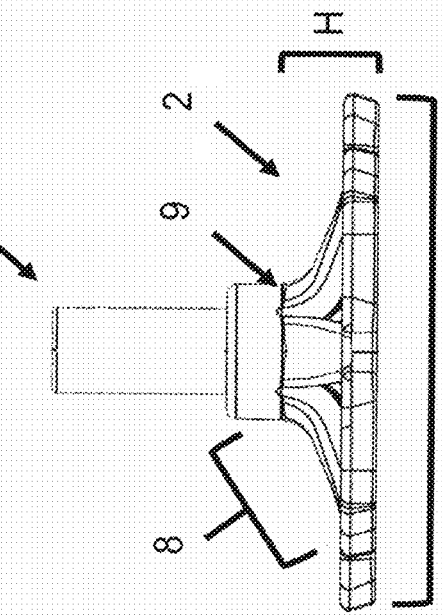

In some embodiments, as shown in FIGS. 2A, 2C, and 2D, the petals 7 of the foot 2 may be curved or include an angled portion 8, such that the point of attachment 9 of the petals 7 to the stem 6 is held at a distance from the apex of the ventricle while the perimeter 10 of the petals 7 is contacting the apex of the ventricle, as shown in FIGS. 2A and 2B. Alternatively, as shown in FIGS. 3A and 3C, the petals 7 may be coupled to the stem 6 at a right angle (90°) to the stem 6, such that the entire perimeter 10 and/or surface area of the petals 7 of the foot 2 may contact the apex of the ventricle.

In some embodiments, as shown in FIGS. 3A-3C, the foot 2 may be used in a ventricular partitioning device for treating acute myocardial infarction in order to prevent cardiac remodeling or damage (configured as an endocardial implant). In this embodiment, the device is configured to be positioned immediately adjacent to the heart wall, for example similar to a patch, across from the region of the infarct.

Figure 4B:
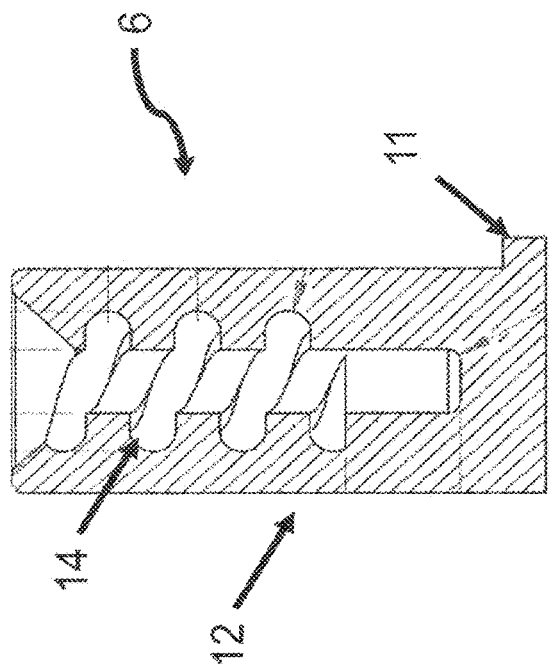
FIGS. 4A-4C illustrate one embodiment of a stem for coupling a membrane to a foot of a ventricular partitioning device.
Figure 4A:
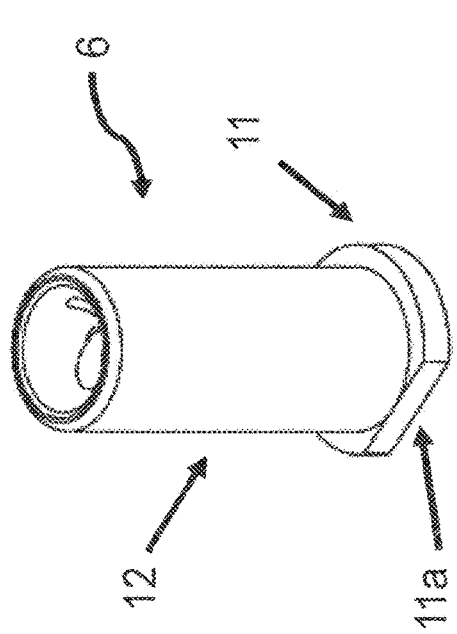
Figure 4C:
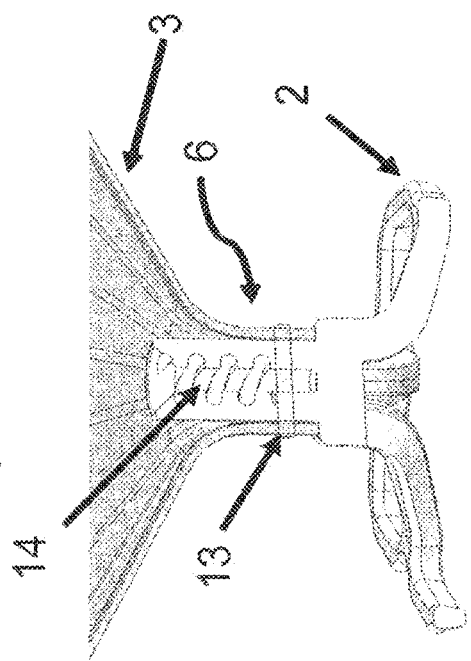

FIGS. 2A-3C illustrate a stem 6 coupled to a foot 2 of a ventricular partitioning device, such that the stem 6 is configured to receive a support frame of a ventricular partitioning device, as shown in FIG. 1. In some embodiments, the stem 6 may be substantially rigid for coupling to the support frame. However, the stem 6 may also be flexible for increasing the elastic recoil force of the ventricular partitioning device. The stem 6, as shown in FIGS. 4A-4C, may include a base 11 and a shaft 12 for receiving a support frame. In some embodiments, as shown in FIG. 4A, the base 11 may include a flange 11a to create a strong bond between the stem 6 and the foot 2 of the ventricular partitioning device. For example, the petals of the foot may be injection molded around the base of the stem and flange. Alternatively, in some embodiments, the stem 6 may be coupled to the foot 2 by another mechanism, for example by screwing, soldering, sintering, snapping, locking, fastening, or any other type of reversible or irreversible coupling mechanism.

FIGS. 4B-4C illustrate a cross-section of a stem 6 of a ventricular partitioning device in accordance with a preferred embodiment. The stem 6 may serve as an interface between the foot 2 and the support frame 3 of the ventricular partitioning device. As shown in FIG. 4C, the foot 2 may be secured to the support frame 3 by a cross pin 13 or any other type of fastener. For example, the hub or shaft at the base of the support frame may slide into the shaft 12 of the stem 6, such that a pin 13 may be inserted through the cross-section of the stem 6 to couple the support frame 3 to the stem 6.

Alternatively, the support frame may be soldered, fastened, glued, or otherwise reversibly or irreversibly coupled to the stem. In some embodiments, the shaft 12 of the stem 6 may be configured to receive a delivery catheter, as described below in association with FIG. 10. For example, the shaft 12 may include helical grooves 14 such that a shaft of the delivery catheter may be screwed into the shaft of the stem 6, as shown in FIGS. 2D, 4B, and 4C.

Figure 5A:
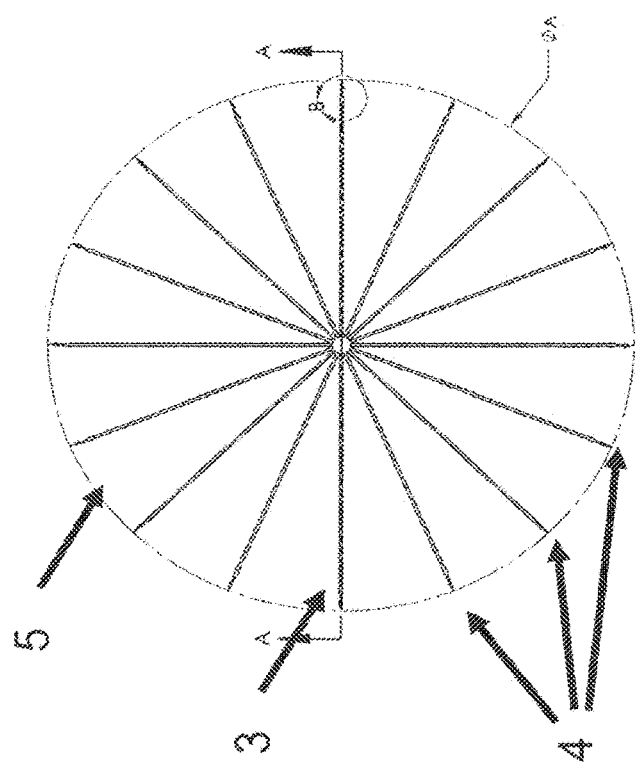
FIGS. 5A and 5B illustrate a top and side view of one embodiment of a membrane coupled to a support frame of a ventricular partitioning device, respectively.
Figure 5B:
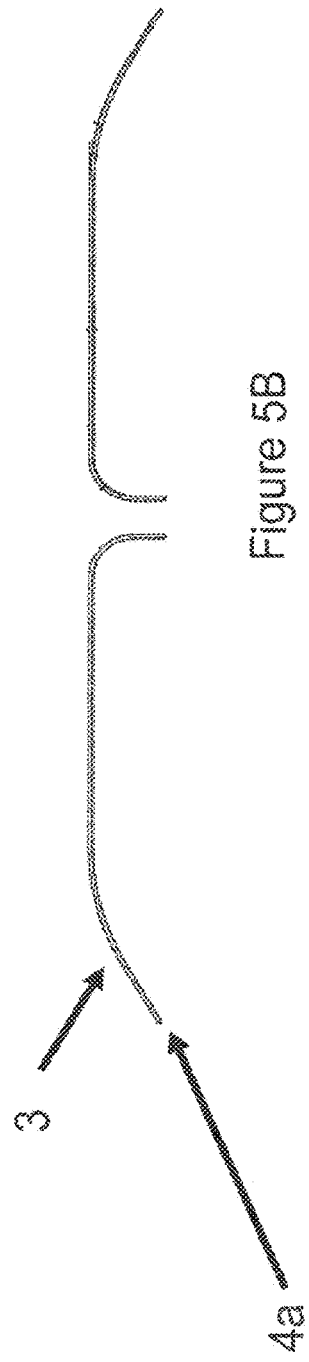

FIGS. 5A and 5B illustrate a top view and side view, respectively, of a membrane 5 coupled to a support frame 3 of a ventricular partitioning device in accordance with a preferred embodiment. The membrane 5 coupled to the support frame 3 is a pressure-receiving surface of the ventricular partitioning device, such that the elastic recoil force of the ventricle is improved when the ventricular partitioning device is implanted. The membrane 5 may be stretched over the struts to give the frame a disk like shape. The membrane 5 may include expanded Polytetrafuoroethylene (ePTFE) having a thickness between 0.01 mm and 1 mm. In one embodiment, the membrane has a thickness of about 0.08 mm. Alternatively, in some embodiments, the membrane 5 may include mesh, or other appropriate permeable, semi-permeable, or impermeable membranes. In some embodiments, the membrane 5 may be formed of a suitable biocompatible polymeric material including Nylon, PET (polyethylene terephthalate) and polyesters such as Hytrel. In some embodiments, the membrane 5 may be porous to facilitate tissue ingrowth after deployment within a patient's heart.

As shown in FIG. 5B, the first free ends 4a of the support frame 3 coupled to the membrane 5 may deflect away from the centerline axis of the ventricular partitioning device when the ventricular partitioning device is deployed in a ventricle. The deflection may improve the anchoring of the ventricular partitioning device to an interior wall of a ventricle.

In some embodiments, as shown in FIGS. 5A, 6A, and 6B, the support frame 3 may, include a plurality of radially expandable struts 4. The struts 4 may be configured to support a membrane 5 coupled to the struts. The struts 4 may improve the elastic recoil properties of the membrane 5 coupled to the struts 4. In some embodiments, the struts 4 may be configured for anchoring the ventricular partitioning device to an interior wall of the ventricle. In some embodiments, the support frame 3 may include 5 struts, 10 struts, 15 struts, or 20 struts. In one embodiment, the support frame 3 includes 16 struts. In some embodiments, each strut 4 may be 1 to 8 cm in length. In one embodiment, each strut 4 has a length of about 3 to 6 cm. In some embodiments, the support frame 3 may be smoothed to a particular surface roughness to reduce trauma to the patient during delivery and improve characteristics of the ventricular partitioning device, such as corrosion resistance and durability. The support frame 3 may be electropolished, chemically treated, and/or mechanically polished by a wheel, tumbling, abrasion, sand blasting, chemical etching, and/or any other method of polishing to achieve a particular surface roughness. In some embodiments, the roughness average (Ra) of the support frame may be between 0.01 μm and 1 μm. In one embodiment, the roughness average (Ra) of the support frame is between about 0.85 μm and 0.15 km.

In some embodiments, as shown in FIGS. 6A-6C, each strut 4 of the support frame 3 may include a first free end 4a and a second end 4b coupled to the foot. The first free end 4a of the support frame 3 may include an anchor or barb 15 for coupling the support frame 3 to an interior wall portion of a heart. This anchoring may allow the ventricular partitioning device to contract and relax with each systolic and diastolic phase, respectively, of the heart cycle. Further, the anchoring may partition the heart into functional and non-functional portions, such that the non-functional portion is proximal to the foot of the ventricular partitioning device.

In some embodiments, as shown in FIGS. 6A-6C, a stop 16 may be located at or near the base of the anchors 15 proximal to the first free end 4a of the struts 4. The stop 16 may be a bulge, projection, or otherwise widening of a portion of the strut 4 near the first free end 4a, which serves to lock the support frame 3 in place and/or reduce or prevent over-penetration of the struts 4 into the ventricle wall. The length of the struts 4 may alternate between a short length strut and a long length strut so that the anchors 15 and/or stops 16 are staggered, which allows the struts 4 to be collapsed into a more compact diameter for delivery.

In some embodiments, as shown in FIG. 6A, each first free end 4a of the strut 4 of the support frame 3 may further include an eyelet 16a. The eyelet 16a may serve as a stop 16, as described above, and/or as a mechanism to couple the membrane to the support frame. During manufacturing, polymer may be melted near the eyelet 16a of the support frame 3 to couple the membrane to the support frame, such that the melted polymer may flow from one side of the strut 4 through the eyelet 16 to the other side of the strut 4 to couple the membrane to the struts 4. As shown in an alternative embodiment in FIGS. 6B-6C, the stop 16, as described above, may be manufactured without an eyelet, such that the polymer melts around the stop 16 and secures the membrane to the support frame 3.

Figure 7A:
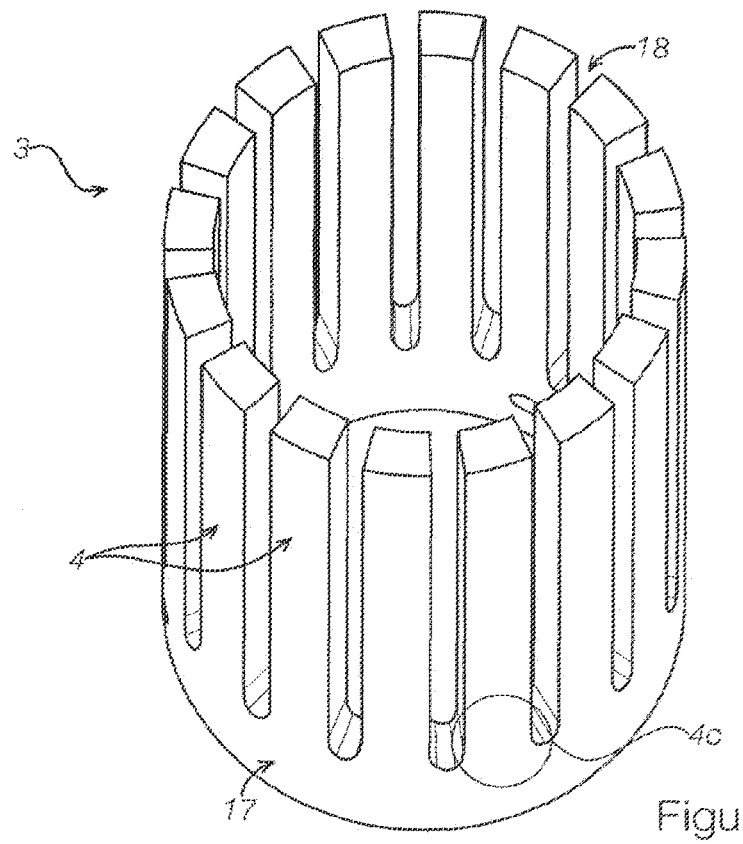
FIGS. 7A-7D illustrate one embodiment of a support frame.

In some embodiments, as shown in FIGS. 7A-7D, the struts may include a material such as, for example, Nitinol, stainless steel, titanium alloys, NiTi alloy, other metal alloys, or plastic composites. In some embodiments, the struts 4 and/or support frame 3 may include a material, which allows for compression of the first free ends towards the central axis during delivery and self expansion upon deployment of the ventricular partitioning device in a patient's heart. In some embodiments, the struts 4 and/or support frame 3 may be cut, for example by a laser, from a tube including Nitinol, stainless steel, or a similar material. During manufacturing, a plurality of longitudinal cuts may extend from one end of the metal tube to a position offset from the other end of the tube, leaving a hub 17 from which the struts 4 extend. The cuts may result in a plurality of slots 18 between the struts 4. In some embodiments, as shown in FIG. 7A, the spacing between the slots 18 may define the strut width W while the thickness of the tube may define the strut thickness T. In some embodiments, the spacing of the slots 18 around the tube may result in struts 4 having a cross-sectional width that is slightly greater than its cross-sectional thickness. This may be accomplished by the slot 18 having a slightly greater spacing than the thickness of the tube. In some embodiments, slightly greater may mean about 1, 2, 3, 4, 5, 10, 15, 20, or 25 percent, or may mean between about 1 to 25 percent, or may mean between about 5 to 20 percent.

Figure 7B:
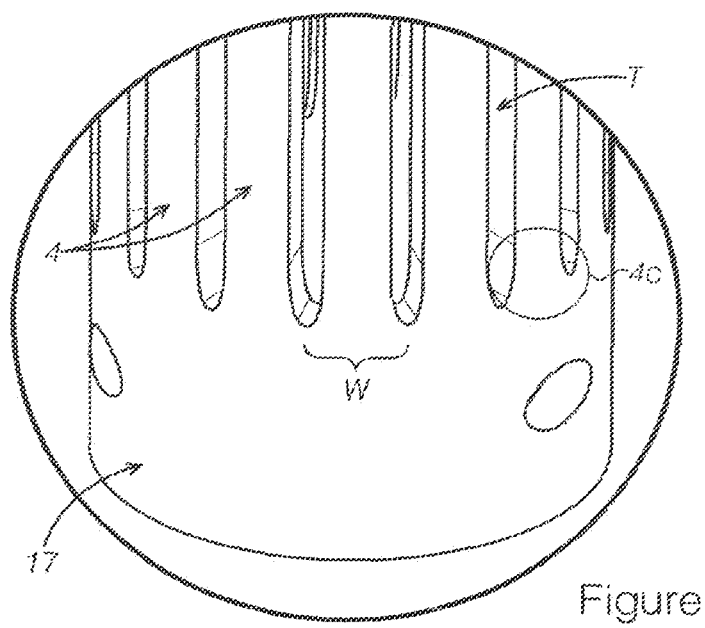

In some embodiments, as shown in FIG. 7B, the base 4c of the strut 4 is the second end of the strut that couples to the foot and extends from the hub 17. The base 4c of the strut 4 may be flared such that the width of the strut 4 increases as it approaches the hub 17. In some embodiments, the flared base 4c may spread bending strains over a larger amount of material, thereby decreasing peak strains during manufacturing, loading of the implant within a catheter, and cyclical use in the ventricle after implantation. In some embodiments, the width of the strut 4 at the hub 17 may be about 5 to 25 percent larger than the width of the strut 4 at a middle portion of the strut 4. In some embodiments, the length of the flared base 4c may be about equal to the width of the flared base 4e at the hub 17. Alternatively, the length of the flared base 4c may be greater than about 5, 10, 15, 20, 25, 30, 35, 40, 45, 50, 75, 100, or 200 percent of the width of the flared base 4c at the hub 17. Alternatively, the length of the flared base 4c may be less than about 95, 90, 85, 80, 75, 70, 65, 60, 55, or 50 percent of the width of the flared base 4c at the hub 17. The flared base may be formed by tapering the slot as it reaches the hub.

Figure 7C:
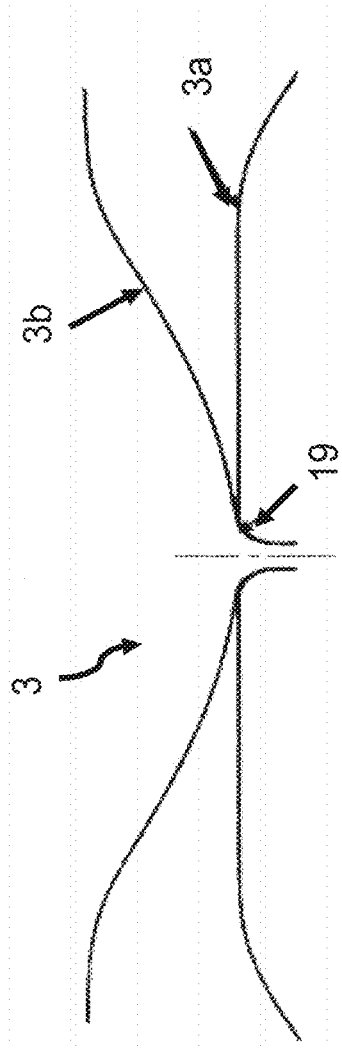

As illustrated in FIG. 7C, in some embodiments, the flared base can have a base bend radius 19 that is sized to (1) reduce or limit peak strains during shape setting to reduce or prevent damage and cracking of the metal frame; (2) reduce or limit peak strains when the implant is loaded into the catheter and reduce or prevent plastic deformation of the metal; and (3) reduce or minimize the height of the implant. In some embodiments, the diameter of the support frame 3 in its free shape 3a can be slightly oversized relative to its laminated shape 3b so that the membrane will stay tight after lamination. For example, the support frame 3 can be oversized by about 3, 4, 5, 6, or 7 mm, or be oversized between about 2 to 10 mm. The lamination mold is designed to conform to the natural shape of the support frame 3 when it is reduced to the lamination diameter 3b. This ensures that the support frame 3 is free to move as designed with little or no alternating strain concentrations.

Figure 7D:
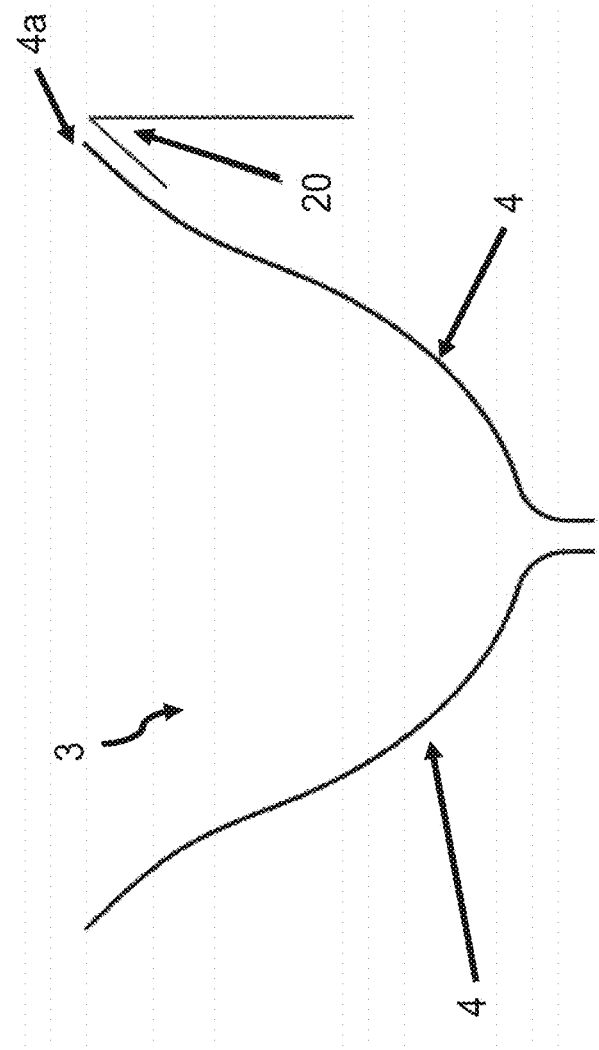

As shown in FIG. 7D, after lamination, there is a strut curvature 20 near the anchor on the free ends 4a of the struts 4 that is designed to optimize the angle of engagement with the left ventricle wall, which improves retention of the implant in the left ventricle. In some embodiments, the strut curvature 20 has a radius of about 0.5 to 1.5 inches. In some embodiments, the angle of engagement is about 30 to 60 degrees.

In some embodiments as described above, the strut cross-section dimensions having a width slightly greater than the thickness, in conjunction with the flared base, may bias the strut so that it deflects outwardly without any significant twist. This may improve the strength of the struts and reduce strain.

Loading and Delivery Systems

Figure 11:
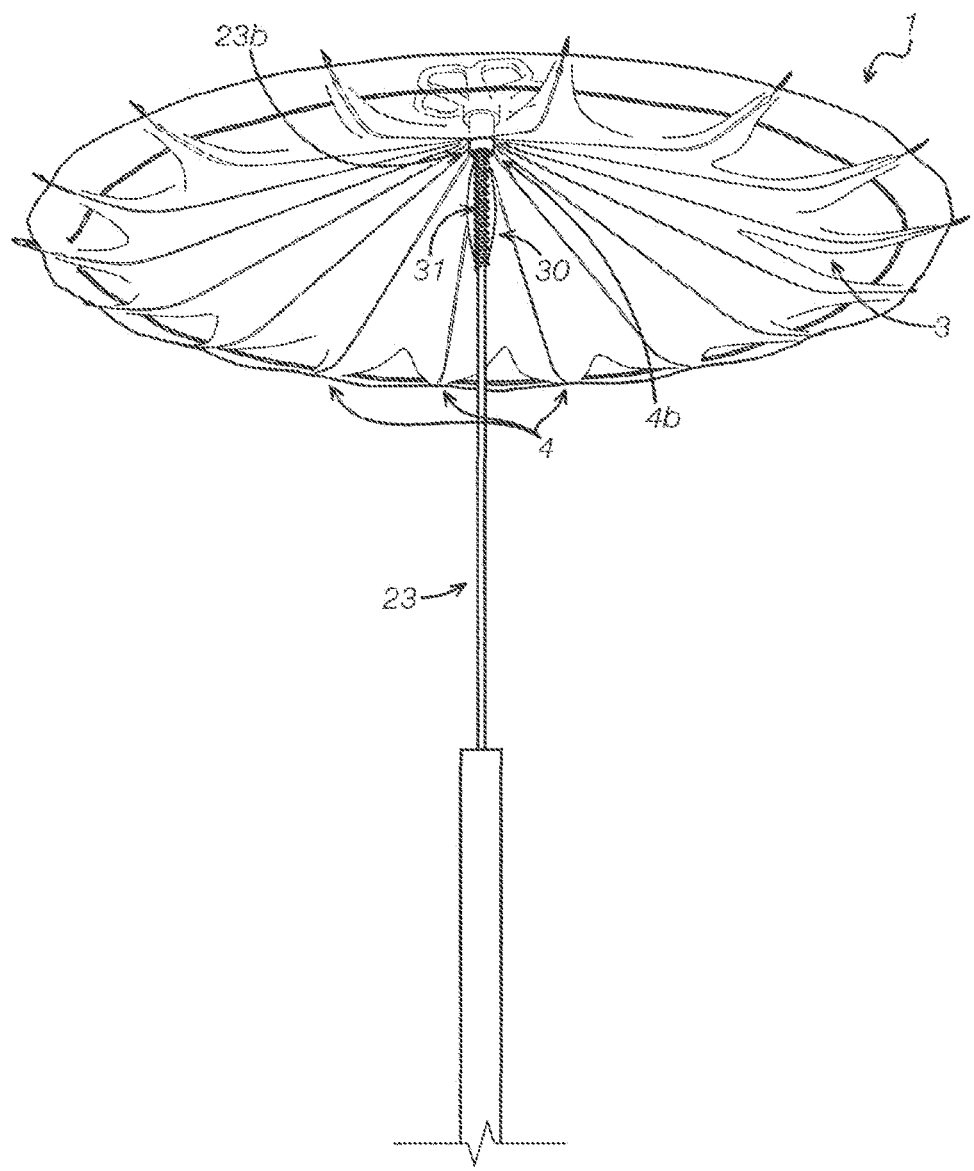
FIG. 11 illustrates one embodiment of a delivery catheter coupled to a ventricular partitioning device.

In some embodiments, a delivery system for a ventricular partitioning device may include an implant loading system, which collapses the ventricular partitioning device into a substantially linear delivery configuration for passage into a guide catheter and into a heart, and which expands the ventricular partitioning device into an umbrella-like shape once the device is delivered into a heart. In some embodiments, the ventricular partitioning device may be delivered transapically, percutaneously, endovascularly, or through any other appropriate means or procedure. In some embodiments, the ventricular partitioning device is coupled to a delivery catheter to facilitate loading into the guide catheter. In some embodiments, the ventricular partitioning device is coupled to a shaft disposed in a lumen of the delivery catheter, for example by screwing the ventricular partitioning device to a shaft in a lumen of the delivery catheter, as shown in FIG. 11.

Described below are two different embodiments of an implant loading system for loading a ventricular partitioning device into a guide catheter. The system as shown in FIGS. 8A-9C requires fewer steps and components as compared to the implant loading system described in FIGS. 10A-10D. However, as evident to one of skill in the art, both implant loading systems may be used to load a ventricular partitioning device into a lumen of a guide catheter for delivery to a heart of a patient.

Figure 8A:
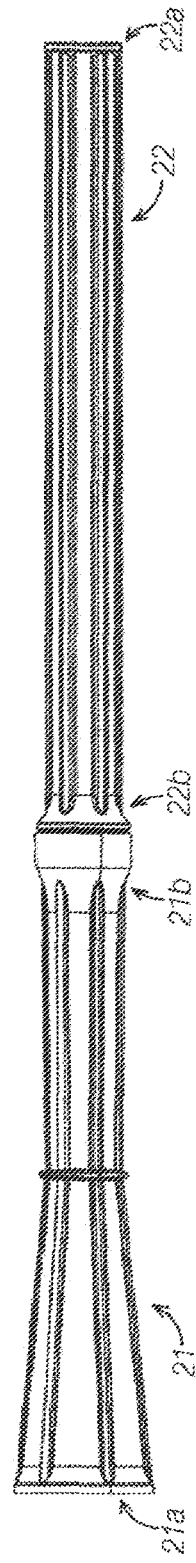
FIGS. 8A-8D illustrate an exterior view of one embodiment of an implant loading system for a ventricular partitioning device.
Figure 8B:
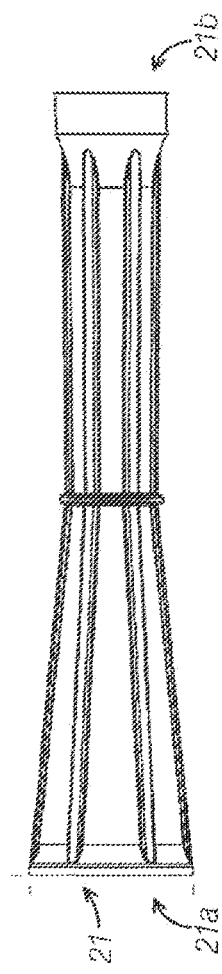
Figure 8C:
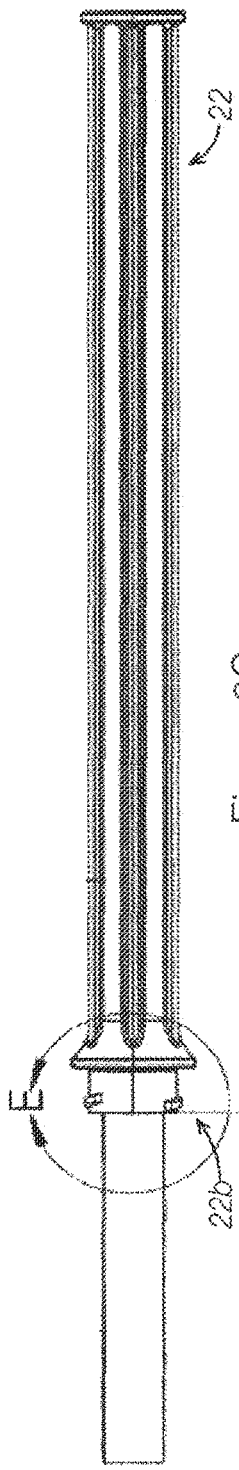
Figure 8D:
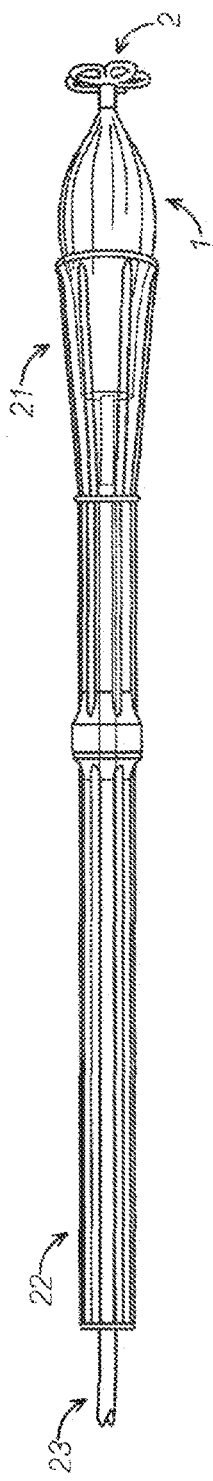

In some embodiments, as shown in FIGS. 8A-9C, an implant loading system for a ventricular partitioning device may include a funnel 21 with a flared first end 21a and a second end 21b, wherein the flared first end 21a is configured for receiving a collapsed ventricular partitioning device 1, as shown in FIGS. 8B and 8D, and a sleeve 22 removably coupled to the second end 21b of the funnel 21, such that the sleeve 22 is configured to transfer the ventricular partitioning device 1 to a guide catheter, as shown in FIGS. 8C and 8D.

FIGS. 8A-8D and 9A-9C illustrate an exterior and cross-sectional view, respectively, of an implant loading system for a ventricular partitioning device, in accordance with a preferred embodiment. As shown in FIGS. 8A-8D, a ventricular partitioning device 1 may be coupled to a delivery catheter 23, as described below. The ventricular partitioning device 1 may be collapsed by drawing at least two sutures, strings, ties, or threads together, such that the diameter of the membrane and thus the ventricular partitioning device is reduced. In this manner, the ventricular partitioning device 1 may be at least partially collapsed around the delivery catheter 23. As used herein, "two sutures, strings, ties, or threads" may refer to two separate sutures, strings, ties, or threads, or two separate ends of a looped suture, string, tie, or thread. In some embodiments, the at least two sutures may be coupled by a tab, such that both sutures may be tensioned and the ventricular partitioning device at least partially collapsed by manipulating the tab.

In some embodiments, the ventricular partitioning device may be positioned in the flared first end 21a of the funnel 21 with the first free ends of the struts of the ventricular partitioning device entering the flared first end 21a of the funnel 21 followed by the foot 2 of the ventricular partitioning device, as shown in FIG. 8D. The funnel 21 may function to fully collapse the ventricular partitioning device for advancement into a lumen of a guide catheter. In some embodiments, as shown in FIG. 8A, the second end 21b of the funnel 21 is removably coupled to a second, distal end 22b of a sleeve 22, for example by threading 33 the funnel 21 onto the second, distal end 22b of the sleeve 22, as shown in FIGS. 8A and 8C. One embodiment of the threads 33 for coupling the funnel 21 to the sleeve 22, as shown in FIG. 9B, is evident using a cross-sectional view of the funnel 21 and sleeve 22, such as shown in FIGS. 9A and 9C. Alternatively, the funnel 21 may be coupled to the sleeve 22 by any suitable mechanism. In some embodiments, the ventricular partitioning device coupled to the delivery catheter 23 may be advanced through the funnel 21 into the sleeve 22 for loading of the ventricular partitioning device into a lumen of a guide catheter. The first, proximal end 22a of the sleeve 22 may include a stop or tapering of the sleeve, such that the ventricular partitioning device does not protrude from the first, proximal end 22a of the sleeve 22 or extend out of the first end 22a of the sleeve 22, as shown in FIGS. 8A-8C. In some embodiments, the interior of the funnel 21 and sleeve 22 may include a smooth surface, for example without flashes or burrs, such that the ventricular partitioning device is not torn or scratched during loading, unloading, and advancing. Once, the ventricular partitioning device is advanced into the sleeve 22 from the funnel 21, the funnel 21 may be uncoupled from the second, distal end 22b of the sleeve 22 and the guide catheter may be coupled in its place.

Figure 12A:
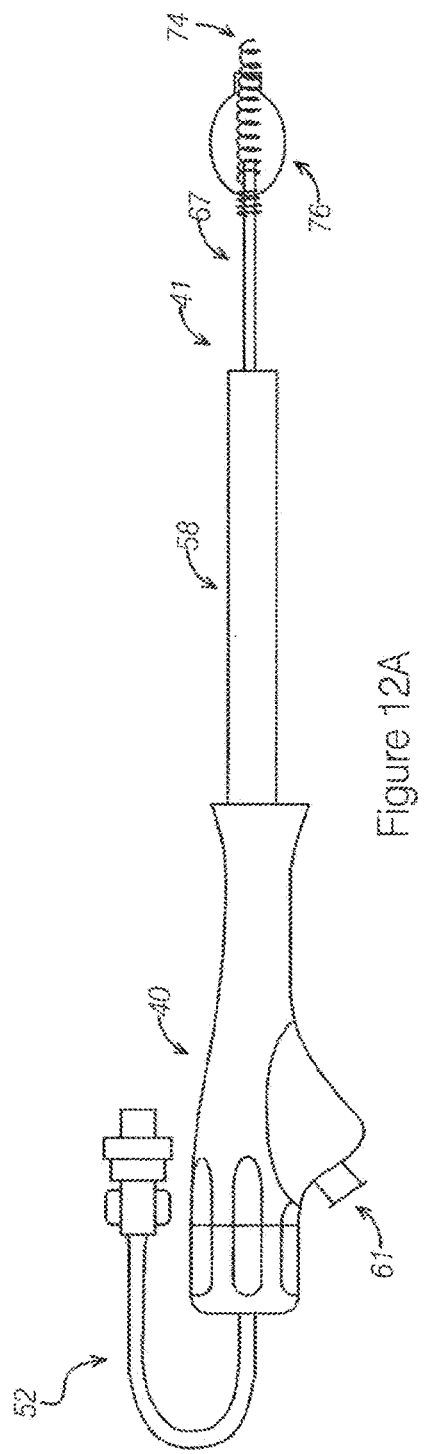
FIG. 12A illustrates one embodiment of a delivery catheter.
Figure 14:
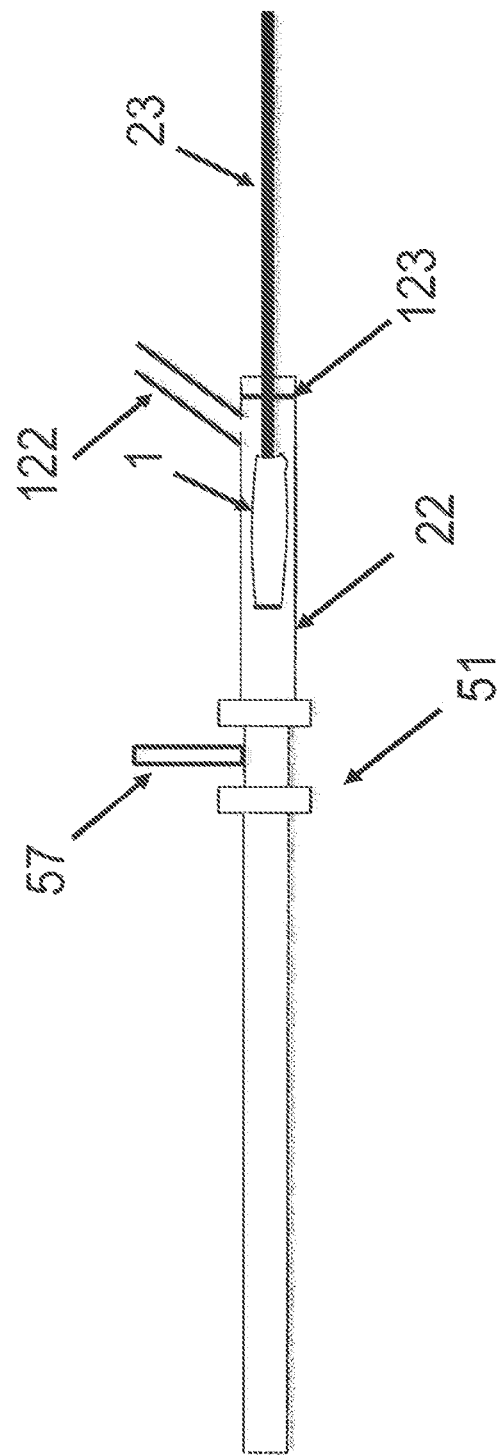
FIG. 14 illustrates another embodiment of a delivery system.

Further, as shown in FIG. 14, in some embodiments, the sleeve 22 may include a fluid delivery port 122, such that fluid, for example saline, may be injected into the sleeve, as described in further detail below. In some embodiments, the fluid is substantially prevented or inhibited from exiting the first or proximal end of the sleeve by a mechanical seal 123 coupled to the first or proximal end 22a of the sleeve 22. The mechanical seal 123 may be, for example, a gasket, O-ring, bung comprising an aperture, bodok seal, hermetic seal, diaphragm seal, labyrinth seal, rotating hemostatic valve, or any other suitable sealing mechanism. For example, as shown in FIG. 12F, the mechanical seal 80 may be a rotating hemostatic valve, which can be rotated to adjust the size of the valve aperture to maintain hemostasis while allowing passage of the delivery catheter and implant through the valve and into the sleeve 22 and guide catheter. In various embodiments, the mechanical seal 123 is sized to contact an inner surface of the sleeve and an outer surface of the delivery catheter 23 to form a liquid-tight or fluid-tight seal. Alternatively, the mechanical seal may be positioned and formed so as to create a liquid-tight or fluid-tight seal by any mechanism known to one skilled in the art. The mechanical seal 123 may be adhered, fastened, or otherwise coupled to the sleeve 22 using any suitable attachment mechanism. Alternatively, the mechanical seal may be integrally molded or otherwise formed with the sleeve.

Figure 15A:
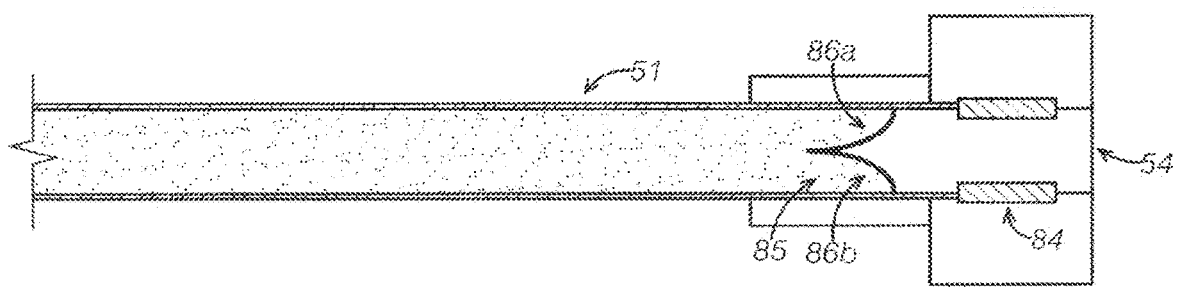
FIG. 15A illustrates one embodiment of guide catheter comprising two hemostatic valves.
Figure 15B:
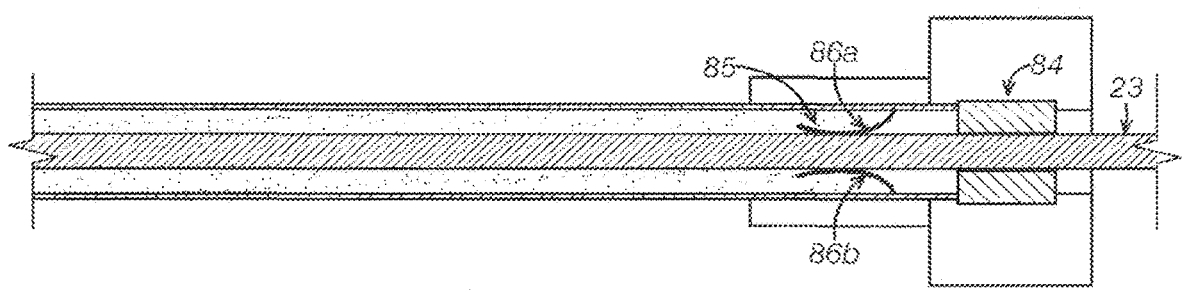
FIG. 15B illustrates one embodiment of a delivery catheter inserted into a guide catheter through two hemostatic valves.

In some embodiments, for example as shown in FIGS. 15A and 15B, the distal end 22b of the sleeve 22 may be coupled to a guide catheter 51. In some embodiments, the distal end 22b of the sleeve 22 may be coupled to a guide catheter 51 using a valve 84, such as a hemostatic valve. The valve 84 may be positioned in the sleeve 22, in the guide catheter 51, or in a separate joint coupling the sleeve 22 to the guide catheter 51, for example a joint (e.g., T-port) comprising a fluid delivery port 57. In some embodiments, the valve 84 may be a rotating valve, which is configured to rotate to increase or decrease the size of the aperture in the valve 84 to allow the passage of the delivery catheter 23 and implant 1 or other medical device through the valve 84 while maintaining a fluid-tight seal around the delivery catheter 23. In some embodiments, the guide catheter 51 can also include a fluid delivery port 57 for introducing fluid into guide catheter.

Additionally or alternatively, in some embodiments, as shown in FIGS. 15A and 15B, the coupling between the guide catheter 51 and the sleeve 22 further includes a second hemostatic valve, such as a check valve or duck-bill valve 85, to reduce or prevent backflow before the delivery catheter 23 is inserted into the guide catheter 51 and the valve is empty. In some embodiments, the check valve or duck-bill valve 85 forms a portion of the guide catheter 51; in other embodiments, the check valve or duck-bill valve 85 forms a portion of a separate joint (e.g., T-port) coupling the sleeve 22 to the guide catheter 51. In some embodiments, the check valve or duck-bill valve 85 covers or seals a proximal end 54 of the guide catheter 51. In one such embodiment, one end of the valve stretches over the proximal end 54 of the guide catheter 51, conforming to its shape, and a second end extends distally into the guide catheter 51. In some such embodiments, a first flap or side 86a and a second flap or side 86b of the check valve or duck-bill valve 85 form complementary surfaces that interlace or interweave when a delivery catheter is not present, as shown in FIG. 15A, and are displaced or splayed open when a delivery catheter is present, as shown in FIG. 15B. In some embodiments, the check valve or duck-bill valve comprises elastic or stretchable material, such that it conforms to the surface of the device or catheter extending through the valve. In some such embodiments, the check valve or duck-bill valve comprises rubber or synthetic elastomer.

The ventricular partitioning device may be advanced from the sleeve into the lumen of the guide catheter. In some embodiments, the delivery catheter 23 coupled to the ventricular partitioning device may be advanced through the guide catheter lumen into a heart of a patient to position the ventricular partitioning device in the heart of the patient. In some embodiments, the sleeve may be removed from the delivery catheter by any suitable mechanism after advancing the ventricular partitioning device into the lumen of the guide catheter. Alternatively, the delivery catheter may be lengthened such that the sleeve may remain on the delivery catheter while the ventricular partitioning device is being positioned in a heart of a patient.

Alternatively, in some embodiments as shown in FIGS. 10A-10D, an implant loading system for a ventricular partitioning device may further include a loader 24 comprising a lumen housing a two-piece introducer 25, referred to herein as a loader introducer pair. Instead of a two-step loading procedure, as shown in FIGS. 8A-9C, the loading procedure shown in FIGS. 10A-10D includes at least two more steps. In some embodiments, as show in FIG. 10A, the funnel 26 for loading the ventricular partitioning device into the sleeve 27 may be truncated as compared to the funnel 21 shown in FIG. 8B. Similar to FIGS. 8A and 8D, the tapered end 26b of the funnel 26 may be coupled to the second end 27b of the sleeve 27 and the ventricular partitioning device coupled to the delivery catheter may be advanced from the funnel 26 into the sleeve 27. In some embodiments, as shown in FIG. 10C, once the ventricular partitioning device is collapsed and advanced through the funnel 26 into the sleeve 27, the funnel 26 may be uncoupled from the second end 27b of the sleeve 27 and the second end 24b of the loader introducer pair 24/25 may be coupled to the second end 27b of the sleeve 27. The loader introducer pair 24/25 may be coupled to the sleeve 27 by a helical screw, latching, snapping, fastening, or any other type of coupling mechanism. The first end 24a of the loader introducer pair 24/25 may be coupled to a guide catheter, such that the lumen of the loader introducer pair is continuous with the lumen of the guide catheter. In some embodiments, as shown in FIG. 10C, the coupling mechanism may include a slot 28 on the loader 24 and a pin, knob, protrusion, or port on the guide catheter, such that the slot 28 receives the pin or port and secures the loader 24 to the guide catheter. Alternatively, the loader 24 may be coupled to the guide catheter by a helical screw, snapping, latching, or any other type of coupling mechanism.

As shown in FIG. 10C, the ventricular partitioning device may be advanced from the sleeve 27 into the loader introducer pair 24/25 and into the guide catheter. The loader 24 may be removed from the system by moving the introducer 25 and delivery catheter through a longitudinal slot 29 in the loader 24. The introducer 25 may be removed from the system by, tearing or axially pulling apart the two halves 25a/25b of the introducer 25, as shown in FIG. 10D, such that the delivery catheter coupled to the ventricular partitioning device in the lumen of the guide catheter remains. In some embodiments, the sleeve 27 may remain on the delivery catheter or be removed. While two embodiments of an implant loading system are described above, any other suitable mechanism may be used and/or substituted by one skilled in the art to deliver a ventricular partitioning device to a heart of a patient.

In some embodiments, as shown in FIG. 11, a system for treating heart failure may include a ventricular partitioning device as described above, and a delivery catheter 23 having a proximal end and a distal end 23b. Further, a system for treating heart failure may include an expansion member 30 near the distal end 23b of the delivery catheter 23 configured to apply pressure to the support frame 3 of the ventricular partitioning device 1 to move the ventricular partitioning device 1 from a collapsed delivery configuration to an expanded deployed configuration, and a coupling element 31 configured to secure the expansion member 30 to the ventricular partitioning device 1 during deployment.

In some embodiments, the expansion member 30 is coupled to the ventricular partitioning device 1 by a coupling element 31 proximal to the second ends 4b of the struts 4 of the support frame 3. In some embodiments, the coupling element 31 includes a helical screw, as shown in FIG. 11. Alternatively, in some embodiments, the coupling element 31 may include a sliding latch, lock, hook, or any other suitable mechanism. In some embodiments, the expansion member 30, for example a balloon, may be in fluid communication with a lumen in the shaft of the delivery catheter 23, such that inflation fluid may be delivered to the interior of the expansion member 30 to inflate the balloon. Alternatively, the balloon may be inflated by a gas, gel, or any other material. The balloon, once inflated, may include a diameter between 30 mm and 45 mm. In one embodiment, the balloon, once inflated, has a diameter of more than or equal to 32 mm.

In some embodiments, the ventricular partitioning device 1 radially expands in the ventricle once delivered to the ventricle. The expansion member 30, coupled to the ventricular partitioning device 1 by a coupling element 31, may be inflated at the distal end of the delivery catheter 23 to fully expand the ventricular partitioning device 1 within the ventricle and to facilitate anchoring the struts 4 of the ventricular partitioning device to an interior wall of the ventricle. Alternatively, in some embodiments, the ventricular partitioning device 1 may expand and anchor sufficiently without the use of the expansion member 30. In some embodiments, rotation of the delivery catheter 23 coupled to the ventricular partitioning device 1 may remove the expansion member 30 and delivery catheter 23 from the ventricular partitioning device 1.

In some embodiments, a delivery system for an implantable ventricular partitioning device includes a delivery catheter, a sleeve, a first fluid delivery port, and a guide catheter. Such devices may include any or all of the features described in the embodiments provided above. In some embodiments, such as shown in FIGS. 12-13, the delivery catheter 52 is formed of a tubular body, or shaft, includes a proximal end and a distal end, and is configured to couple to a ventricular partitioning device or other implantable device. The implant loader sleeve 22 of various embodiments defines a lumen configured to receive the delivery catheter 52 and the implantable device, as previously described above. In some embodiments, the first fluid delivery, port 61 is positioned on the delivery catheter 52, as illustrated in FIG. 12A, and/or a fluid deliver port can be located on the sleeve 22, as shown in FIG. 14, and a mechanical seal 42 is coupled to the sleeve 22. For example, the mechanical seal 42 can be a gasket or other sealing device, as further described herein, that is located in the proximal end of the sleeve 22. The mechanical seal 42 of some embodiments is sized to contact an inner surface of the sleeve 22 and an outer surface of the delivery catheter 52 to form a liquid-tight seal. In some embodiments, the guide catheter 51 is formed of a tubular body having a proximal end, a distal end, a lumen extending therethrough for receiving the delivery catheter 52, and a second fluid delivery port 57 positioned thereon. In various embodiments, the proximal end of the guide catheter 51 is connected to the distal end of the sleeve 22. In some embodiments, the fluid delivery ports can be opened and closed by, for example, using a valve or by clamping the lines supplying fluid to the ports.

The system, as shown in FIGS. 12-13, functions to maintain the implantable device (e.g. ventricular partitioning device) relatively free of blood during implantation, reduce or prevent the flow of blood back into the delivery system during implantation of the ventricular partitioning device, reduce friction between the ventricular partitioning device and the delivery, system, and/or facilitate easy opening of the ventricular partitioning device in the ventricle.

In some embodiments, delivering fluid through the first and/or second fluid delivery ports, for example at a positive pressure, creates a first pressure in the guide catheter that is greater than a second pressure in the ventricle. Such fluid delivery is shown with two fluid delivery arrows in FIG. 12B. The resulting increased pressure in the guide catheter may reduce or prevent blood from flowing backward into the guide catheter and onto the ventricular partitioning device. It has been found that in at least some embodiments, deployment of the device in the ventricle is achieved more easily with more consistent and effective results when it does not get loaded down with blood during the implantation process.

In some embodiments, the positive pressure of fluid delivery is about 150-200, 200-250, 250-300 mm Hg, or any other suitable pressure. In some embodiments, the first pressure is between 200 and 600 mm Hg, and preferably 200-400 mm Hg, and the second pressure is between 0 and 300 mm Hg, and preferably 75-175 mm Hg. In some embodiments, the first pressure is about 200-250, 250-300, 300-350, 350-400, 400-450, 450-500, 500-550, or 550-600 mm Hg, and the second pressure is about 5-100, 100-150, 150-200, 200-250, or 250-300 mm Hg. In one embodiment, the first pressure is about 300 mm Hg and the second pressure is about 120 mm Hg. In some embodiments, the fluid can be delivered at a positive pressure using a pressurized fluid reservoir, such as a pressurized IV bag, for example.

Alternatively, in some embodiments, the fluid can be delivered at a predetermined rate using a pump. The flow rate of fluid through the catheter can be about 30-120 mL/min, or about 0.5-5 mL/sec, or about 0.5, 1.0, 1.5, or 2.0 mL/sec. In some embodiments, the flow rate can be adjusted by the operator.

In some embodiments, the injection of fluid through the first and/or second fluid delivery ports may alternatively or additionally function to remove bubbles from the delivery system. For example, the first fluid delivery port of the delivery catheter can be used to introduce fluid while the second fluid delivery port, which can be located on the guide catheter, can be used to aspirate any trapped gas bubbles. Generally, the bubbles can be aspirated using a fluid delivery port that is distal to the implant. Alternatively, the delivery system as described may be used in any suitable catheterization and/or implantation procedure or method.

As shown in FIGS. 12A and 13, the delivery catheter 52 includes a proximal end 40 and a distal end 41. The distal end 41 of the delivery catheter 52 is configured to couple to an implantable device, for example a ventricular partitioning device, as described above. In some embodiments, the delivery catheter 52 has an outer shaft 58 with an interior (i.e., lumen) 59, and an adapter 60 at a proximal end with a first fluid delivery port 61. The first fluid delivery port 61 is in fluid communication with the interior 59 of the outer shaft 58 of the delivery catheter for delivery of fluid, for example heparinized saline, into the delivery system. Alternatively, in some embodiments, the first fluid delivery port may be positioned on the sleeve configured to receive the implantable device coupled to the delivery catheter, as described above in FIG. 14.

Further, the delivery catheter 52 may include a torque shaft 67. The torque shaft 67, preferably formed from hypotubing (e.g., stainless steel or superelastic NiTi) and having an inner lumen 68, is rotatable and disposed within an inner lumen 69 of the inner shaft 62 of the delivery catheter 52. The torque shaft 67 may be secured at a proximal end 70 of the delivery catheter 52 within an adapter 71 with a rotating knob 72. In some such embodiments, an inflation port 73, proximal to the rotating knob 72, is in fluid communication with the inner lumen 68 of the torque shaft 67. A coupling element 74, for example a helical coil screw, is secured to a distal end 75 of the torque shaft 67. Rotation of the torque knob 72 on the proximal end 70 of the torque shaft 67 rotates the coupling element 74 on the distal end 75 of the torque shaft 67 to facilitate deployment of the implantable device 30. An expansion member 76, for example an inflatable balloon, is secured at its proximal end 77 to the torque shaft 67 at a location proximal to the distal end 75 of the torque shaft 67. In some embodiments, the expansion member 76 is secured to the torque shaft 67 by an adhesive or other fastening mechanism in a manner that creates a fluid-tight seal. The expansion member 76 has an interior 79 in fluid communication with the inner lumen 68 of the torque shaft 67. Inflation fluid may be delivered to the interior 79 of the expansion member 76 through the port 73. Inflation of the expansion member 76 by delivering inflation fluid through the port 73 facilitates opening of the implantable device in the ventricle, which in turn facilitates securement of the implantable device 30 to the heart wall.

Figure 12B:
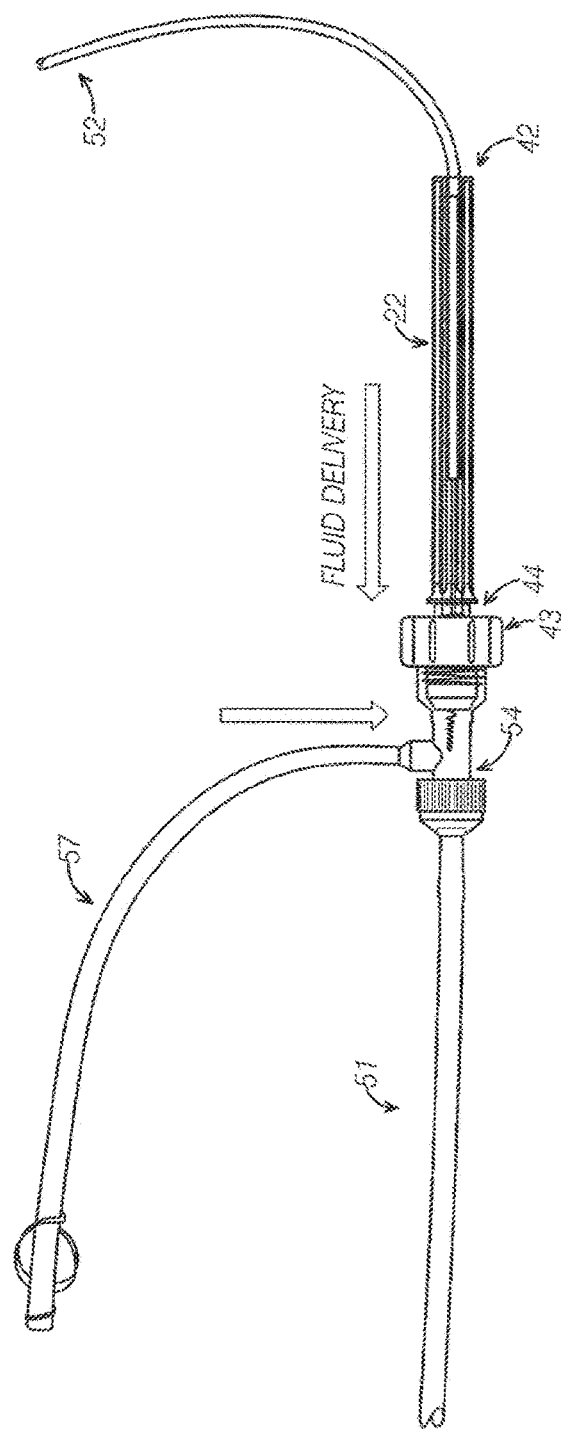
FIG. 12B illustrates one embodiment of a delivery system.
Figure 12C:
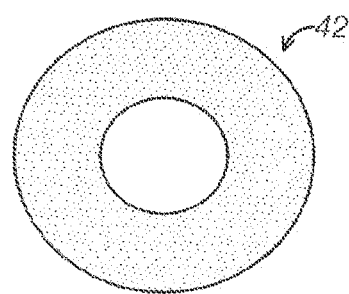
FIGS. 12C-12E illustrate one embodiment of a gasket.
Figure 12D:
Figure 12E:
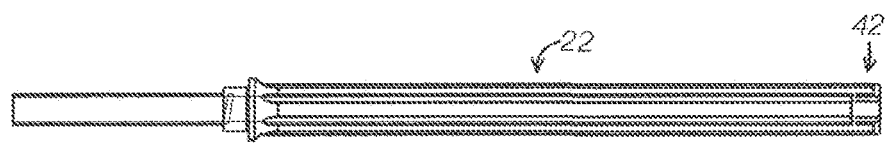
Figure 12F:
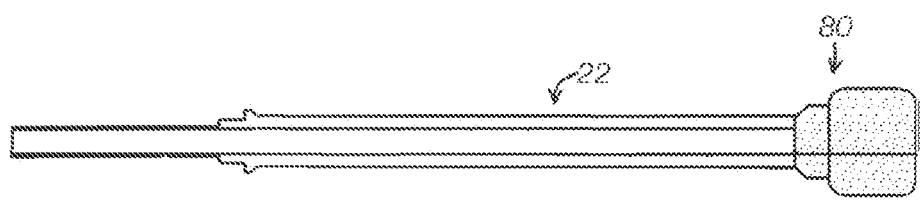
FIG. 12F illustrates one embodiment of a hemostatic valve.
Figure 13:
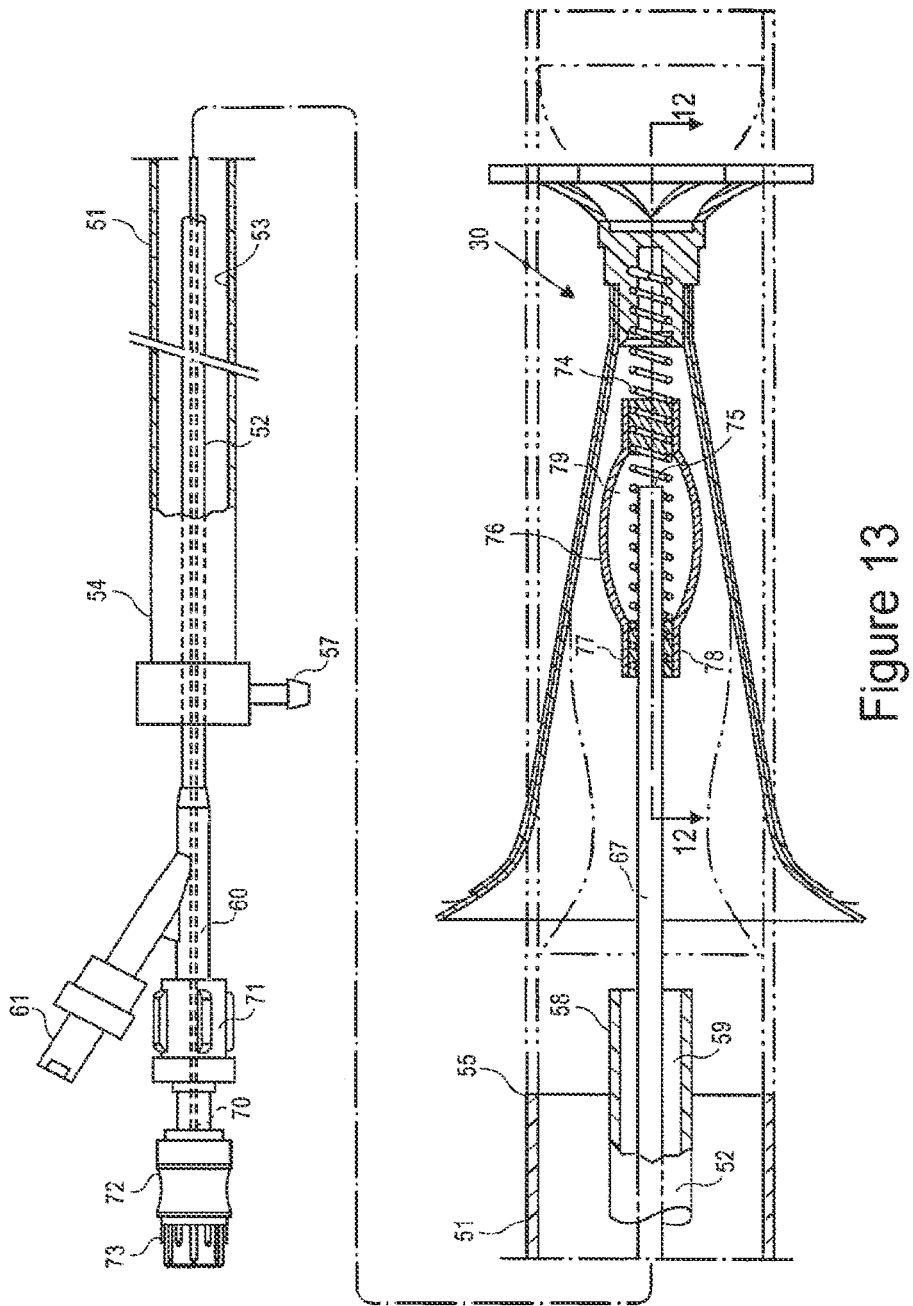
FIG. 13 illustrates one embodiment of a delivery catheter positioned in a guide catheter.

In some embodiments, the mechanical seal 42, as shown in FIGS. 12B-12E, functions to create a liquid-tight or fluid-tight seal between the sleeve 22 and the delivery catheter 52, such that there is reduced loss of liquids from the delivery system. FIG. 12B illustrates the sleeve 22 attached to the guide catheter 51 and the delivery catheter 52 inserted into and through the sleeve 22. FIG. 12C illustrates a front view of an embodiment of the mechanical seal 42 with an opening for removably receiving the delivery catheter 51. FIG. 12D is a cross-sectional view and FIG. 12E is a side view of an embodiment of the sleeve with a mechanical seal 42. The mechanical seal 42 is coupleable to the sleeve 22. In some embodiments, the mechanical seal 42 is sized and positioned to contact an inner surface of the sleeve 22 and an outer surface of the outer shaft 58 of the delivery catheter 52 while the implantable device coupled to the delivery catheter is positioned in the sleeve 22. The mechanical seal may include a gasket, O-ring, bung including an aperture, bodok seal, hermetic seal, diaphragm seal, labyrinth seal, or any other type of seal known to one of skill in the art. The mechanical seal 42 can be located at the proximal end of the sleeve 22. The mechanical seal 42 can be elastic or partially elastic, such as around the opening of the seal, in order to conform to and form a fluid tight seal around the delivery, catheter 52.

In some embodiments, as shown in FIGS. 12B-13, the guide catheter 51 functions to receive a ventricular partitioning device from the sleeve 22 and position the ventricular partitioning device in a ventricle. The guide catheter 51 includes a tubular body defining an inner lumen 53 extending between a proximal end 54 and a distal end 55. The proximal end 54 of the guide catheter 51 is coupled to the distal end 44 of the sleeve 22, for example through a connector, a hemostatic valve 43, or any other type of valve. In some embodiments, the guide catheter 51 further includes a second fluid delivery port 57 on the proximal end 54 of the guide catheter 51. The second fluid delivery port 57 is configured for injecting fluids, for example heparinized saline, through the guide catheter. The second fluid delivery port 57 is in fluid communication with the inner lumen 53 of the guide catheter 51.

Methods

As shown in FIG. 16 a method of preparing a ventricular partitioning device for implantation using a delivery system includes: coupling the ventricular partitioning device to a delivery catheter S100; loading the ventricular partitioning device and a portion of the delivery catheter into a sleeve and creating a liquid-tight seal between a portion of the sleeve and the delivery catheter S110; coupling a distal end of the sleeve to a guide catheter S120; and delivering fluid through a first fluid delivery port disposed on the delivery catheter or the sleeve and/or delivering fluid through a second fluid delivery port disposed on the guide catheter S130. In various embodiments, delivering the fluid creates a first pressure in the guide catheter that is greater than a second pressure in a ventricle. The method of FIG. 16 functions to maintain the ventricular partitioning device relatively free of blood during implantation, reduce or prevent the flow of blood back into the delivery system during implantation of the ventricular partitioning device, reduce friction between the ventricular partitioning device and the delivery system, and facilitate easy opening of the ventricular partitioning device in the ventricle. Alternatively, the methods described may be used in any suitable catheterization and/or implantation procedure or method.

As shown in FIG. 16, one embodiment of preparing a ventricular partitioning device for implantation using a delivery system includes block S100, which recites coupling the ventricular partitioning device to a delivery catheter. S100 functions to attach, screw, adhere, or otherwise fasten the ventricular partitioning device to the delivery catheter. As described above, in one embodiment, the delivery catheter may include a helical screw at the distal tip configured for mating with threads in the stem of the ventricular partitioning device. Alternatively, any other coupling mechanism may be utilized.

As shown in FIG. 16, one embodiment of preparing a ventricular partitioning device for implantation using a delivery system includes block S110, which recites loading the ventricular partitioning device and a portion of the delivery catheter into a sleeve and creating a liquid-tight or fluid-tight seal between a portion of the sleeve and the delivery catheter. In the loaded configuration, the ventricular partitioning device is positioned in the sleeve and the delivery catheter extends out of the first or proximal end of the sleeve. A mechanical seal coupled to the proximal end of the sleeve may create the liquid-tight or fluid-tight seal between the sleeve and the delivery catheter, such that any liquid or fluid injected into the delivery system is substantially maintained in the delivery system. In various embodiments, the delivery catheter or the sleeve includes a first fluid delivery port positioned thereon. S110 functions to prepare a ventricular partitioning device for implantation, for example by collapsing the ventricular partitioning device using the sleeve and positioning the ventricular partitioning device for transfer into a guide catheter. As described above, a funnel may be coupled to the sleeve to facilitate loading of the ventricular partitioning device into the sleeve. In some such embodiments, the ventricular partitioning device coupled to the delivery catheter may be loaded first free ends first into the flared end of the funnel and advanced from the funnel into the sleeve. The funnel may be removed from the sleeve, and as described below, a guide catheter may be coupled in its place at the distal end of the sleeve.

As shown in FIG. 16, one embodiment of preparing a ventricular partitioning device for implantation using a delivery system includes block S120, which recites coupling a distal end of the sleeve to a guide catheter. S120 functions to prepare the ventricular partitioning device for advancement from the sleeve to the guide catheter for delivery into a ventricle. The sleeve of some embodiments is coupled to a valve, such as a hemostatic valve, on the proximal end of the guide catheter. The guide catheter of some embodiments has a second fluid delivery port positioned thereon. In some embodiments, the method includes advancing the ventricular partitioning device coupled to the delivery catheter through one or more valves (e.g., hemostatic valve, check valve, duck-bill valve, etc.) on the proximal end of the guide catheter into the tubular body of the guide catheter.

As shown in FIG. 16, one embodiment of preparing a ventricular partitioning device for implantation using a delivery system includes block S130, which recites delivering fluid through at least one of the first fluid delivery port or the second fluid delivery port, such that delivering the fluid creates a first pressure in the guide catheter that is greater than a second pressure in a ventricle. S130 functions to reduce or prevent blood backflow into the delivery system during implantation of the ventricular partitioning device. Further, flushing the delivery system with saline reduces blood accumulation on the ventricular partitioning device resulting in improved expansion of the ventricular partitioning device upon implantation in the ventricle. In some embodiments, the first pressure is between 200 and 600 mm Hg, and preferably 200-400 mm Hg, and the second pressure is between 0 and 300 mm Hg, and preferably 75-175 mm Hg. The first pressure created in the guide catheter of other embodiments is about 200-250, 250-300, 300-350, 350-400, 400-450, 450-500, 500-550, or 550-600 mm Hg. In one embodiment, the first pressure is about 300 mm Hg. The second pressure in the ventricle of some embodiments is about 5-100, 100-150, 150-200, 200-250, or 250-300 mm Hg. In one embodiment, the second pressure is about 120 mm Hg. In some embodiments, the fluid, for example heparinized saline, is delivered at a positive pressure into the first and/or second fluid delivery ports, such that the pressure in the guide catheter prevents or substantially prevents blood from flowing backwards into the guide catheter, while continued distal movement of the delivery catheter through the guide catheter pushes the ventricular partitioning device out of the guide catheter and into the ventricle. Alternatively, the first and/or second fluid delivery ports may be utilized to remove bubbles from the delivery system, for example, by opening the fluid delivery ports to the atmosphere.

In some embodiments, a method of preparing a ventricular partitioning device for implantation further includes: transferring the ventricular partitioning device from the sleeve to the guide catheter; positioning with a delivery catheter a ventricular partitioning device near an apex of a patient's ventricle; delivering the ventricular partitioning device from the guide catheter into the ventricle; expanding an expansion member coupled to the partitioning device to apply pressure to the plurality of expandable struts to expand the partitioning device; and uncoupling the delivery catheter from the ventricular partitioning device, as described above. In some embodiments, a method of delivering a ventricular partitioning device may further include positioning a delivery sheath over the partitioning device to collapse the partitioning device for removal or redeployment of the partitioning device.

In some embodiments, a method of preparing a ventricular partitioning device for implantation further includes allowing blood from the patient's body to enter the guide catheter through the distal end of the guide catheter and exit the guide catheter through the second fluid delivery port disposed on the guide catheter. This step may occur prior to and/or as the ventricular partitioning device is advanced from the sleeve into the guide catheter. Allowing the backflow of blood into the guide catheter and out the second fluid delivery port removes any air that may be present between the second fluid delivery port and the ventricular partitioning device as the ventricular partitioning device is advanced into the guide catheter.

Further, in some embodiments, delivering fluid through at least one of the first fluid delivery port or the second fluid delivery port includes pushing or otherwise introducing fluid, for example saline, into the guide catheter using the first fluid delivery port disposed on the delivery catheter or the sleeve. In some such embodiments, the fluid is substantially maintained in the guide catheter by the fluid-tight or liquid-tight seal, for example the seal established by the mechanical seal. This fills the space behind the ventricular partitioning device with saline as the ventricular partitioning device is advanced, preventing air from being drawn into the guide catheter.

In some embodiments, a method of preparing a ventricular partitioning device for implantation further includes closing, sealing, or otherwise blocking the second fluid delivery port disposed on the guide catheter after the ventricular partitioning device is advanced distally beyond the second fluid delivery port of the guide catheter. This may ensure, for example, that the saline or other fluid delivered via positive pressure through the first fluid delivery port is not expelled through the second delivery port but rather advances through the guide catheter.

As used in the description and claims, the singular form "a", "an" and "the" include both singular and plural references unless the context clearly dictates otherwise. For example, the term "a fluid delivery port" may include, and is contemplated to include, a plurality of fluid delivery ports. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a device or method consisting essentially of the elements as defined herein would not exclude other materials, features, or steps that do not materially affect the basic and novel characteristic(s) of the claimed invention. "Consisting of"

shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. A delivery system for an implantable device, the system comprising:
   a delivery catheter comprising a tubular body having a proximal end and a distal end and an interior lumen, wherein the delivery catheter is configured to couple to the implantable device;
   a sleeve defining a lumen configured to receive the delivery catheter and the implantable device coupled thereto;
   a first fluid delivery port positioned on the delivery catheter and in fluid communication with the interior lumen of the delivery catheter; and
   a guide catheter comprising a tubular body having a proximal end configured to connect to the sleeve and for the delivery catheter to be inserted into from the sleeve, a distal end, an interior lumen configured to receive the delivery catheter, and a second fluid delivery port positioned on the guide catheter and in fluid communication with the interior lumen of the guide catheter and configured to be in fluid communication with the interior lumen of the delivery catheter and the first fluid delivery port when the delivery catheter is positioned within the interior lumen of the guide catheter, and
   wherein the second fluid delivery port is configured to aspirate gas from the interior lumen of the guide catheter while fluid is delivered through the first fluid delivery port, or the first fluid delivery port is configured to aspirate gas from the interior lumen of the delivery catheter while fluid is delivered through the second fluid delivery port.

2. The system of claim 1, further comprising a pressurized fluid reservoir configured to be in fluid communication with the delivery catheter.

3. The system of claim 1, further comprising a pump configured to deliver fluid through the delivery catheter.

4. The system of claim 1, further comprising the implantable device, and wherein the implantable device is an expandable device having a support frame.

5. The system of claim 1, wherein the first fluid delivery port and/or the second fluid delivery port are configured to deliver fluid creating a first pressure in the guide catheter of about 200-600 mm Hg.

6. The system of claim 1, wherein the guide catheter further comprises a hemostatic valve positioned at the proximal end of the guide catheter.

7. The system of claim 1, wherein the first fluid delivery port and/or the second fluid delivery port are configured to deliver fluid creating a positive pressure in the guide catheter.

8. The system of claim 1, further comprising a funnel, wherein the funnel comprises a flared first end and a second end, wherein the flared first end is configured for receiving and collapsing the implantable device, and wherein the second end is coupleable to the sleeve.

9. The system of claim 8, wherein the second end of the funnel is configured to be removed from a distal end of the sleeve prior to the distal end of the sleeve connecting to the proximal end of the guide catheter.

10. The system of claim 1, further comprising a first valve positioned at the proximal end of the guide catheter and configured for the delivery catheter to pass through.

11. The system of claim 10, wherein the first valve is a rotating valve.

12. The system of claim 10, wherein the first valve is configured to connect the proximal end of the guide catheter to a distal end of the sleeve.

13. The system of claim 10, further comprising a second valve positioned at the proximal end of the guide catheter and configured for the delivery catheter to pass through.

14. The system of claim 13, wherein the second valve is configured to reduce fluid backflow before the delivery catheter is inserted into the proximal end of the guide catheter.

15. The system of claim 14, wherein the guide catheter includes a T-port, and the first valve, the second valve, and the second fluid delivery port are each positioned on the T-port.

16. The system of claim 1, further comprising a third fluid delivery port positioned on the sleeve and in fluid communication with the lumen of the sleeve.

17. The system of claim 16, wherein the third fluid delivery port is configured to be in fluid communication with the interior lumen of the guide catheter and the second fluid delivery port when the sleeve is connected to the guide catheter.

18. The system of claim 17, wherein the third fluid delivery port is configured to be in fluid communication with the interior lumen of the delivery catheter when the sleeve is connected to the guide catheter and the delivery catheter is positioned within the lumen of the sleeve and the interior lumen of the guide catheter.

19. The system of claim 1, wherein the first fluid delivery port is configured to introduce fluid into the interior lumen of the guide catheter when the delivery catheter is positioned within the interior lumen of the guide catheter.

20. The system of claim 1, wherein the sleeve includes a proximal end and a distal end, the proximal end of the sleeve configured for the delivery catheter to be inserted into, and the distal end of the sleeve is configured to be connected to the proximal end of the guide catheter.

* * * * *